(12) United States Patent
Pitha et al.

(10) Patent No.: US 8,563,522 B2
(45) Date of Patent: Oct. 22, 2013

(54) METHOD OF MAINTAINING AND/OR ATTENUATING A DECLINE IN QUALITY OF LIFE

(75) Inventors: Josef Pitha, Rockville, MD (US); George S Roth, Pylesville, MD (US); Michael Griffin Hayek, Dayton, OH (US); Stefan Patrick Massimino, Portland, OR (US); Michael Anthony Ceddia, Mexico (MX); Gary Mitchell Davenport, Dayton, OH (US); John Russell Burr, Clay Township, OH (US)

(73) Assignees: The IAMS Company, Cincinnati, OH (US); GeroScience, Inc., Pylesville, MD (US)

( * ) Notice: Subject to any disclaimer, the term of this patent is extended or adjusted under 35 U.S.C. 154(b) by 700 days.

(21) Appl. No.: 12/371,101

(22) Filed: Feb. 13, 2009

(65) Prior Publication Data

US 2009/0253642 A1 Oct. 8, 2009

Related U.S. Application Data

(63) Continuation-in-part of application No. 11/313,199, filed on Dec. 20, 2005, now abandoned, which is a continuation-in-part of application No. 09/950,052, filed on Sep. 12, 2001, now abandoned, which is a continuation-in-part of application No. 08/889,877, filed on Jul. 8, 1997, now abandoned.

(51) Int. Cl.
*A61K 31/70* (2006.01)

(52) U.S. Cl.
USPC .................................. 514/23; 424/725

(58) Field of Classification Search
USPC .................................. 514/23; 424/725
See application file for complete search history.

(56) References Cited

U.S. PATENT DOCUMENTS

| | | |
|---|---|---|
| 2,540,979 A | 2/1951 | Clymer et al. |
| 2,641,548 A | 6/1953 | Heinrich |
| 3,320,130 A | 5/1967 | Henry |
| 3,398,001 A | 8/1968 | Benson |
| 3,431,338 A | 3/1969 | Munzel |
| 3,677,898 A | 7/1972 | Mitsugi et al. |
| 3,898,132 A | 8/1975 | Hettrick |
| 3,957,974 A | 5/1976 | Hata |
| 4,248,857 A | 2/1981 | DeNeale et al. |
| 4,314,995 A | 2/1982 | Hata et al. |
| 4,332,790 A | 6/1982 | Sozzi et al. |
| 4,338,346 A | 7/1982 | Brand |
| 4,399,163 A | 8/1983 | Brennan et al. |
| 4,411,925 A | 10/1983 | Brennan et al. |
| 4,423,029 A | 12/1983 | Rizzi |
| 4,434,231 A | 2/1984 | Jung |
| 4,518,696 A | 5/1985 | Gerhman et al. |
| 4,592,748 A | 6/1986 | Jost |
| 4,647,453 A | 3/1987 | Meismer |
| 4,767,623 A | 8/1988 | Conway et al. |
| 4,781,939 A | 11/1988 | Martin et al. |
| 4,797,289 A | 1/1989 | Reddy |
| 4,806,368 A | 2/1989 | Reddy |
| 4,808,626 A | 2/1989 | Friedman et al. |
| 4,814,193 A | 3/1989 | Shenouda et al. |
| 4,816,259 A | 3/1989 | Matthews et al. |
| 4,859,377 A | 8/1989 | Shasha et al. |
| 4,935,247 A | 6/1990 | Marttila et al. |
| 5,096,717 A | 3/1992 | Wirth et al. |
| 5,132,137 A | 7/1992 | Reimann et al. |
| 5,160,745 A | 11/1992 | DeLuca et al. |
| 5,171,580 A | 12/1992 | Imartino et al. |
| 5,286,495 A | 2/1994 | Batich et al. |
| 5,322,686 A | 6/1994 | Grahn et al. |
| 5,344,824 A | 9/1994 | Ohkuma et al. |
| 5,389,389 A | 2/1995 | Beck |
| 5,413,960 A | 5/1995 | Dobrogosz et al. |
| 5,518,733 A | 5/1996 | Lamothe et al. |
| 5,531,988 A | 7/1996 | Paul |
| 5,540,945 A | 7/1996 | Ikushima |
| 5,569,634 A | 10/1996 | Miller et al. |
| 5,629,017 A | 5/1997 | Pozzi et al. |
| 5,726,161 A | 3/1998 | Whistler |
| 5,733,540 A | 3/1998 | Lee |
| 5,766,520 A | 6/1998 | Bronshtein |
| 5,785,990 A | 7/1998 | Langrehr |
| 5,824,779 A | 10/1998 | Koegel et al. |

(Continued)

FOREIGN PATENT DOCUMENTS

| | | |
|---|---|---|
| AU | 19928098 A1 | 7/1999 |
| CA | 1300538 | 5/1992 |
| CA | 2256256 | 6/2000 |
| DE | 3715070 A1 | 11/1988 |
| DE | 19819475 A1 | 4/1989 |
| DE | 4018392 A1 | 12/1991 |
| DE | 19860375 A1 | 12/1998 |
| EP | 0168112 | 1/1986 |
| EP | 0298605 A1 | 11/1989 |
| EP | 0298605 B1 | 11/1989 |

(Continued)

OTHER PUBLICATIONS

Victora J. et al. Effect of Ingested Mannoheptulose in Animals and Man. Metabolism 18(2)87-102, Feb. 1969.*

(Continued)

*Primary Examiner* — Ralph Gitomer

(74) *Attorney, Agent, or Firm* — Amy M. Foust

(57) ABSTRACT

Methods of maintaining and/or attenuating a decline in the quality of life of a mammal comprising the step of administering to the mammal a composition comprising an effective amount of mannoheptulose wherein the effective amount of mannoheptulose provides a dosage to the mammal on a daily basis from about 0.001 gram per kilogram of body weight of the mammal to about 1 gram per kilogram of body weight of the mammal.

34 Claims, 11 Drawing Sheets

(56) References Cited

U.S. PATENT DOCUMENTS

| | | | |
|---|---|---|---|
| 5,849,327 A | 12/1998 | Berliner et al. | |
| 5,853,697 A | 12/1998 | Strober et al. | |
| 5,854,067 A | 12/1998 | Newgard et al. | |
| 5,871,794 A | 2/1999 | Brito | |
| 5,910,447 A | 6/1999 | Lawrence et al. | |
| 5,939,117 A | 8/1999 | Chen et al. | |
| 5,976,579 A | 11/1999 | McLean | |
| 6,007,808 A | 12/1999 | DeHaen et al. | |
| 6,033,888 A | 3/2000 | Batich et al. | |
| 6,133,323 A | 10/2000 | Hayek | |
| 6,309,666 B1 | 10/2001 | Hatano et al. | |
| 6,310,090 B1 | 10/2001 | Hayck | |
| 6,358,555 B1 | 3/2002 | Takahashi | |
| 6,406,853 B1 | 6/2002 | Spindler | |
| 6,586,027 B2 | 7/2003 | Axelrod et al. | |
| 6,737,089 B2 | 5/2004 | Wadsworth et al. | |
| 6,893,662 B2 | 5/2005 | Dittmar et al. | |
| 6,896,914 B2 | 5/2005 | Chapnick et al. | |
| 6,932,990 B2 | 8/2005 | Konishi et al. | |
| 6,979,675 B2 | 12/2005 | Tidmarsh | |
| 7,097,831 B1 | 8/2006 | Bengs et al. | |
| RE39,436 E | 12/2006 | Spindler et al. | |
| 7,666,459 B2 * | 2/2010 | Hayek et al. | 426/635 |
| 2001/0018048 A1 | 8/2001 | Leer et al. | |
| 2001/0018071 A1 | 8/2001 | Cochran et al. | |
| 2002/0035071 A1 | 3/2002 | Pitha et al. | |
| 2002/0098235 A1 | 7/2002 | Dittmar et al. | |
| 2003/0092669 A1 | 5/2003 | Chapnick et al. | |
| 2003/0104090 A1 | 6/2003 | Levy et al. | |
| 2003/0157166 A1 | 8/2003 | Chen et al. | |
| 2003/0170217 A1 | 9/2003 | Collins et al. | |
| 2003/0190309 A1 | 10/2003 | Zink et al. | |
| 2004/0001875 A1 | 1/2004 | Sunvold et al. | |
| 2004/0022882 A1 | 2/2004 | Picirilli et al. | |
| 2004/0047896 A1 | 3/2004 | Malnoe et al. | |
| 2004/0167229 A1 | 8/2004 | Bakker-Arkema et al. | |
| 2004/0175389 A1 | 9/2004 | Porubcan | |
| 2004/0228933 A1 | 11/2004 | Chapnick | |
| 2005/0013849 A1 | 1/2005 | Lemaure et al. | |
| 2005/0074519 A1 | 4/2005 | Bartnick et al. | |
| 2005/0096256 A1 | 5/2005 | Sinclair | |
| 2005/0100617 A1 | 5/2005 | Malnoe et al. | |
| 2005/0106133 A1 | 5/2005 | Zink et al. | |
| 2005/0112259 A1 | 5/2005 | Qvyjt | |
| 2005/0152884 A1 | 7/2005 | Boileau et al. | |
| 2005/0158293 A1 | 7/2005 | Boileau et al. | |
| 2005/0158294 A1 | 7/2005 | Boileau et al. | |
| 2005/0164978 A1 | 7/2005 | Chapnick et al. | |
| 2005/0175598 A1 | 8/2005 | Boileau et al. | |
| 2005/0208163 A1 | 9/2005 | Brovelli et al. | |
| 2005/0249837 A1 | 11/2005 | Massimino et al. | |
| 2005/0249841 A1 | 11/2005 | Hayek et al. | |
| 2005/0266438 A1 | 12/2005 | Spindler et al. | |
| 2006/0088517 A1 | 4/2006 | Kriegler et al. | |
| 2006/0100162 A1 | 5/2006 | Pitha et al. | |
| 2006/0116330 A1 | 6/2006 | Pitha et al. | |
| 2007/0149466 A1 | 6/2007 | Milburn et al. | |
| 2007/0220619 A1 | 9/2007 | Zhao-Wilson | |
| 2007/0231371 A1 | 10/2007 | Pan et al. | |
| 2007/0231414 A1 | 10/2007 | Aoki et al. | |
| 2008/0113921 A1 | 5/2008 | Piccirilli et al. | |
| 2008/0176935 A1 | 7/2008 | Henderson et al. | |
| 2008/0194476 A1 | 8/2008 | Piccirilli et al. | |
| 2008/0214479 A1 | 9/2008 | Pitha et al. | |
| 2008/0260696 A1 | 10/2008 | Massimino et al. | |
| 2008/0260866 A1 | 10/2008 | Massimino et al. | |
| 2008/0279786 A1 | 11/2008 | Cash | |
| 2009/0252834 A1 * | 10/2009 | Hayek et al. | 426/66 |

FOREIGN PATENT DOCUMENTS

| | | |
|---|---|---|
| EP | 0366621 A1 | 2/1990 |
| EP | 0353581 A2 | 7/1990 |
| EP | 0391416 A1 | 10/1990 |
| EP | 0399819 A2 | 11/1990 |
| EP | 0439315 B1 | 7/1991 |
| EP | 0627173 A1 | 7/1994 |
| EP | 0659769 A2 | 6/1995 |
| EP | 0659769 B1 | 6/1995 |
| EP | 0399819 B1 | 10/1995 |
| EP | 0508701 B1 | 10/1995 |
| EP | 0850569 A1 | 1/1998 |
| EP | 0862863 B1 | 9/1998 |
| EP | 0956858 A1 | 11/1999 |
| EP | 0956858 B1 | 11/1999 |
| EP | 1010372 A2 | 6/2000 |
| EP | 0850569 B1 | 12/2000 |
| EP | 1312667 A1 | 5/2003 |
| EP | 1 637 041 B1 | 4/2008 |
| FR | 2668081 A1 | 4/1992 |
| FR | 2615203 A1 | 11/1998 |
| GB | 1190387 | 5/1970 |
| GB | 1595054 | 8/1976 |
| GB | 2241421 A | 4/1991 |
| GB | 2252228 A | 5/1992 |
| GB | 2245492 A | 8/1992 |
| GB | 2311027 A | 9/1997 |
| JP | 62201823 | 9/1987 |
| JP | 03076561 | 4/1991 |
| JP | 94256170 A | 9/1994 |
| JP | 96242763 A | 9/1996 |
| JP | 2000-191519 | 11/2000 |
| JP | 01278781 A | 10/2001 |
| RU | 2123343 C1 | 12/1998 |
| WO | WO 88/08452 A1 | 11/1988 |
| WO | WO 89/05849 A1 | 6/1989 |
| WO | WO 91/17672 A1 | 11/1991 |
| WO | WO 93/02558 A1 | 2/1993 |
| WO | WO 94/04180 A2 | 3/1994 |
| WO | WO 94/04180 A3 | 3/1994 |
| WO | WO 94/21284 A1 | 9/1994 |
| WO | WO 95/03809 A2 | 2/1995 |
| WO | WO 95/07090 A1 | 3/1995 |
| WO | WO 95/34292 A2 | 3/1995 |
| WO | WO 96/01612 A1 | 1/1996 |
| WO | WO 96/38159 A1 | 1/1996 |
| WO | WO 97/09448 A1 | 3/1997 |
| WO | WO 97/16198 A1 | 5/1997 |
| WO | WO 97/20577 A1 | 6/1997 |
| WO | WO 98/19968 A1 | 5/1998 |
| WO | WO 98/23727 A1 | 6/1998 |
| WO | WO 98/27967 A1 | 7/1998 |
| WO | WO 98/35014 A2 | 8/1998 |
| WO | WO 98/35014 A3 | 8/1998 |
| WO | WO 98/47374 A1 | 10/1998 |
| WO | WO 98/54982 A1 | 12/1998 |
| WO | WO 99/09839 A1 | 3/1999 |
| WO | WO 99/11245 A1 | 3/1999 |
| WO | WO 99/20745 A1 | 4/1999 |
| WO | WO 99/30576 A1 | 6/1999 |
| WO | WO 99/48372 A1 | 9/1999 |
| WO | WO 99/51108 A1 | 10/1999 |
| WO | WO 99/51108 A1 | 10/1999 |
| WO | WO 99/52511 A1 | 10/1999 |
| WO | WO 00/06127 A1 | 2/2000 |
| WO | WO 00/06127 A1 | 2/2000 |
| WO | WO 00/27364 A1 | 5/2000 |
| WO | WO 00/41707 A2 | 7/2000 |
| WO | WO 00/42168 A2 | 7/2000 |
| WO | WO 00/57712 A1 | 10/2000 |
| WO | WO 01/12164 A1 | 2/2001 |
| WO | WO 01/90311 A1 | 12/2001 |
| WO | WO 01/93011 A3 | 12/2001 |
| WO | WO 02/083879 A2 | 10/2002 |
| WO | WO 03/007732 A2 | 1/2003 |
| WO | WO 03/010297 A1 | 2/2003 |
| WO | WO 03/010298 A1 | 2/2003 |
| WO | WO 03/010299 A1 | 2/2003 |
| WO | WO 03/045356 A1 | 6/2003 |
| WO | WO 2004/100670 A1 | 11/2004 |
| WO | WO 2005/115421 A | 4/2005 |

(56) References Cited

FOREIGN PATENT DOCUMENTS

| WO | WO 2007/009111 A1 | 1/2007 |
|---|---|---|
| WO | WO 2007/057439 A | 5/2007 |
| WO | WO 2007/137808 A1 | 12/2007 |

OTHER PUBLICATIONS

Blatherwick N. et al. Metabolism of Mannoheptulose, Excretion of the Sugar After Eating Avocado. J Biol Chem 133:643-650, 1940.*
Roe J. et al. Further Studies of the Physiological Availability of Heptoses. J Biol Chem 121:37-43, 1937.*
Fajans S. et al. Stimulation of Insulin Release in the Dog . . . J of Clinical Endocrinology and Metabolism 33(1)35-41, Jul. 1971.*
Raonimalala A. et al. Action of Soluble Carbohydrates from Avocado Fruit on Utilization of Calcium in the Rat. Ann Nutr Aliment 34(4)735-44, 1980.*
Viktora J. et al. Effect of Ingested Mannoheptulose in Animals and Man. Metabolism Clincal and Experimental 18(2)87-102, Feb. 1969.*
Adeyemi et al, "Analgesic and Anti-Inflammatory Effects of the Aqueous Extract Leaves of *Persea americana* Mill (Lauraceae)" Fitoterapia, IDB Holding, Milan, IT, vol. 73, No. 5, Aug. 1, 2002, pp. 375-380, XP002318086.
C V Mosby, "Avocado sugars are effective inducer of cutaneous defensive functions" Journal of the American Academy of Dermatology, St Louis MO, US, vol. 50, No. 2, Feb. 1, 2007 p. AB84, XP005937005.
Burger et al., "Cardiomyopathy in Ostriches (*Struthio camelus*) Due to Avocado 9*Persea americana* Var. Guatemalensis) Intoxication", *Journal of the South African Veterinary Association*, vol. Jaargang 65 No. 2, Jun. 1994.
Byung Pal Yu et al., "Modulation of Aging Processes by Dietary Restriction", *CRC Press*, Boca Raton (1994).
Cullen et al. , "Inhibition of glucose metabolism in pancreatic cancer induces cytotoxicity via metabolic oxidative stress" Gastroenterology, vol. 128, No. 4 supp. 2, Apr. 2005 pp. A483, XP002495963.
Carranza J et al, Database EMBASE (Online) Elsevier Science Publishers, Amsterdam, NL, Nov. 2004, "Lower quantities of avocado as daily source of monounsaturated fats: Effect on serum and membrane lipids, endothelial function, platelet aggregation and C-reactive protein in patients with metabolic syndrome" XP002485347.
Ekor et al., "Protective effect of the methanolic leaf extract of *Persea anericana* (avocado) against paracetamol-induced acute hepatotoxicity in rats" International Jornal of Pharmacology, Asian Network for Scientific Information, vol. 2, No. 4, Jan. 1, 2006, pp. 416-420, XP001538905.
F. B. La Forge, Absorption and Effect of Ingested Mannoheptulose, *Nutrition Reviews*, vol. 27, No. 7 1969.
Facchini et al., Insulin Resistance As A Predictor of Age-Related Diseases, *The Journal of Clinical Endocrinology & Metabolism*, 86(8): 3574-3578 , 2001.
Francesconi et al., "5-Thio-D-Glucose: Hypothermic Responses in Mice", *Am. J. Physiology*, 239(3) R214-R218, 1980.
Guo et al. , "In Vivo 2-Deoxyglucose Administration Preserves Glucose and Glutamate Transport and Mitochondrial Function in Cortical Synaptic Terminals After Exposure to Amyloid Beta-Peptide and Iron: Evidence for a Stress Response" Experimental Neurology, Academic Press, vol. 166. No. 1, Jan. 1, 2000, XP008056810 pp. 173-179.
Kalant et al., "Effect of Diet Restriction on Glucose Metabolism and Insulin Responsiveness in Aging Rats", Mechanisms of Ageing and Development, 46 (1988) 89-104.
Kealy et al., "Effects of Diet Restriction on Life Span and Age-Related Changes in Dogs", *JAVMA*, vol. 220, No. 9, May 1, 2002.
Koizumi et al., "Influences of Dietary Restriction and Age on Liver Enzyme Activities and Lipid Peroxidation in Mice" 1987 *American Institute of Nutrition*, Jul. 1986.
Kurata et al., "Structural Evaluation of Glucose Analogues on Feeding Elicitation in Rat", *Metabolism*, vol. 38, No. 1 Jan. 1989: pp. 46-51.

Lane et al., "2-Deoxy-D-Glucose Feeding in Rats Mimics Physiologic Effects of Calorie Restriction", *Journal of Anti-Aging Medicine*, vol. 1, No. 4, 1998.
Lane et al., "Calorie Restriction in Nonhuman Primates: Implications for Age-Related Disease Risk", *Journal of Anti-Aging Medicine*, vol. 1, No. 4, 1998.
Lane et al., "Calorie Restriction Lowers Body Temperature in Rhesus Monkeys, Consistent With a Postulated Anti-Aging Mechanism in Rodents", *Proc. Natl. Acad. Sci.*, vol. 93 pp. 4159-4164, Apr. 1996.
Lawrence Fishbein et al., Biological Effects of Dietary Restriction, *Springer-Verlag*, 1991.
Liu et al., "'Hass' Avocado Carbohydrate Fluctuations. I. Growth and Phenology", *J. Amer. Soc. Hort. Sci.* 124(6): 671-675. 1999.
Liu et al., "'Hass' Avocado Carbohydrate Fluctuations. II. Fruit Growth and Ripening", *J. Amer. Soc. Hort. Sci.*, 124(6): 676-681. 1999.
Liu et al., "Postulated Physiological Roles of the Seven-Carbon Sugars, Mannoheptulose, and Perseitol in Avocado", *J. Amer. Soc. Hort. Sci.*, 127 (1): 108-114, 2002.
Masoro et al., "Dietary Restriction Alters Characteristics of Glucose Fuel Use", *Journal of Geronotology*, Biological Sciences 1992, vol. 47, No. 6 B202-B208.
McKay et al., "The Effect of Retarded Growth Upon the Length of Life Span and Upon the Ultimate Body Size", *J. Nutr.*, vol. 10, pp. 63-79 (1935).
Meyer et al., "Effects of D-mannoheptulose and Its Hexaacetate Ester on Hormonal Secretion From the Perfused Pancreas", *International Journal of Molecular Medicine*, 6: 143-152, 2000.
Naveh et al., "Defatted Avocado Pulp Reduces Body Weight and Total Hepatic Fat But Increases Plasma Cholesterol in Male Rats Fed Diets wWth Cholesterol", *American Society for Nutritional Sciences*, 2002, pp. 2015-2018.
Sutton et al, Nutrigenomics New Zealand, "Considerations for successful development and launch of personalized nutrigenomic foods" Mutation Research, Amsterdam, NL, vol. 622. No. 1-2, Aug. 8, 2007, pp. 117-121, XP022191854.
Poehlman et al., "Caloric Restriction Mimetics: Physical Activity and Body Composition Changes", *Journals of Geronotology*: Series A 2001, vol. 56A (Special Issue I): 45-54.
Ramsey et al., "Dietary Restriction and Aging in Rehesus Monkeys: The University of Wisconsin Study", *Experimental Gerontology*, 35 (2000) 1131-1149.
Rezek et al., "Glucose Antimetabolites and Hunger", 106: 143-157, 1975.
Roth et al., "Caloric Restriction in Primates and Relevance to Humans", *Laboratory of Neurosciences, Geronotology Research Center, National Institute on Aging, National Institutes of Health Pages*, 307-315, 2001.
Scarbrough et al. "2-deoxy-D-glucose and 17-(allylamino)-17-demethoxygeldanamycin enhances toxicity as well as increases parameters indicative od oxidative stress" Free Radical Biology and Medicine, Elsevier Science, vol. 43, No. suppl. 1, Nov. 14, 2007, p. S59, XP009105389.
Sener et al., "D-mannoheptulose Uptake and Its Metabolic and Secretory Effects in Human Pancreatic Islets", *International Journal of Molecular Medicine*, 6: 617-620, 2000.
Shaw et al., "High Performance Liquid Chromatographic Analysis of d-manno-Heptulose, Perseitol, Glucose, and Fructose in Avocado Cultivars", *J. Agric. Food. Chem.* 1980, 28, 379-382.
Simons et al. "2-deoxy-D-gulcose (2DG) enhances cispalatin cytotoxicity in human head and neck cancer cells via metabolic oxidative stress" Free Radical Biology and Medicine, vol. 41, No. suppl. 1, Nov. 15, 2006, pp. S112-S113, XP009105143.
Sakata et al., "Feeding Modulation by Pentose and Hexose Analogues[1-3]", *Am. J. Clin Nutr 1992*: 55:272S-7S
Viktora, et al., "Effect of Ingested Mannopheptulose in Animals and Man", *Metabolism*, 1969, vol. 18, No. 2, pp. 87-102.
Weindruch et al., "The Retardation of Aging and Disease by Dietary Restriction", *Charles S. Thomas* (1988).
Molly T. Kibenge et al., Identification of Biochemical Defects in Pancreatic Islets of fa/fa Rats: A Development Study—Obesity Research, vol. 3, No. 2, Mar. 1995.

(56) References Cited

OTHER PUBLICATIONS

Bela Issekutz, Jr., et al., "Effects of Manno-Heptulose on Glucose Kinetics in Normal and Gluco-Corticoid Treated Dogs"—Life Sciences, vol. 13, pp. 635-643, Jun. 11, 1974.

Morishita Jintan KK, "Yogurt for Supply Physiologically Important Intestinal Bacteria—Contains Bacteria Contained in Capsule Having Inner Layer Made of Digestible Substance and Outer Layer Dissolving in Intestine," MORI, Abstract, Mar. 10, 1995.

O'Callaghan et al., "Differential Cytokine Response of Cells Derived from Different Lymphoid Compartments to Commensal and Pathogenic Bacteria," Departments of Microbiologoy and Medicine, University College, Mercy Hospital Cork, Ireland, Dept. of Surgery, Mercy Hospital Cork Ireland, 2000.

O'Halloran et al., "Adhesion of Potential Probiotic Bacteria to Human Epithelial Cell Lines," Departments of Microbiologoy and Medicine, University College, Mercy Hospital Cork, Ireland, Dept. of Surgery, Mercy Hospital Cork Ireland, 2000.

O'Mahony et al., Probiotic Bacteria and Pathogenic Bacteria Elicit Differential Cytokine Responses From Dendritic Cells, XP-001097379, pp. 1625, 2000.

O'Mahony et al., "Probiotic Impact on Microbial Flora, Inflammation and Tumour Development in IL-10 Knockout Mice," Aliment Pharmacol Ther, vol. 15, pp. 1219-1225, 2001.

O'Mahony et al., "Probiotic Bacteria and the Human Immune System," Dept. Microbiology and Medicine, National Food Biotechnology Centre, University College Cork & Dept. Surgery, Mercy Hospital, Cork Ireland, 2000.

Panwala et al., "A Novel Model of Inflammatory Bowel Disease: Mice Deficient for the Multiple Drug Resistance Gene, mdrla, Spontaneously Develop Colitis," The American Association of Immunologists, The Journal of Immunology, vol. 161, pp. 5733-5744, 1998.

Rogler et al., "Cytokines in Inflammatory Bowel Disease," World Journal of Surgery, vol. 22, pp. 382-389, XP002296948, 1998.

Yu "Modulation of Aging Processes by Dietary Restriction", 1994.

Roth et al., Annals New York Academy of Science 928, pp. 305-315, 2001.

Scardovi, V. "Irregular Nonsporing Gram-Positive Rods," Genus Bifidobacterium Orla-Jensen, 472 ann, 1924.

Schmitt et al., "The Immunostimulatory Function of IL-12 in T-Helper Cell Development and Its Regulation by TGF-B, IFN-y and IL-4," Chem. Immunet Basel Karger, vol. 68, pp. 70-85, 1997.

Shimada, N., "Significance of 1, 5-Anhydro-D-Glucitol in Diabetes Mellitus Management," Sangyo Igaku, vol. 36, No. 6, pp. 448-449. (As provided by the US PTO in Office Action dated Sep. 9, 2004, for U.S. Appl. No. 09/950,052.), 1994.

SNOW Brand Milk Products, "Enteric Capsules—Comprising Core Containing Drug etc. and Coating of Hardened Oil of M. Pt. Higher than Body Temp. and Disintegrated by Lipase in Intestine," SNOW, Mar. 31, 1986, Abstract.

Stagg et al., "The Dendritic Cell: It's Role in Intestinal Inflammation and Relationship with Gut Bacteria," www. Gutjnl.com, 2003.

Stallmach et al., "Induction and Modulation of Gastrointestinal Inflammation," Trends Immunology Today, vol. 19, No. 10, pp. 438-441, Oct. 1998.

Strober et al., "Reciprocal IFN-gamma and TFG-Beta Responses Regulate the Occurrence of Mucosal Inflammation," Immunol. Today, vol. 2, pp. 61-64, Feb. 18, 1997.

Takeda Chemical Ind KK, "Dry Coated Tablet—Comprises Core Tablets Containing Enzyme Prepn. In Enteric Films Within Outer Shell," TAKE, Abstract, May 10, 1982.

Van Damme et al., "The Proportion of Th 1 Cells, Which Prevail in Cut Mucosa, is Decreased in Inflammatory Bowel Syndrome," Blackwell Science Ltd. Clinical and Experimental Immunology, vol. 125, pp. 383-390, 2001.

Voet, Donald and Judith G., Biochemistry, John Wiley' & Sons, Inc. pp. 1044-1045, 1995.

Wein et al., "Analyzing A Bioterror Attack on the Food Supply: The Case of Botolinum Toxin in Milk," The National Academy of Sciences of the USA, 2005.

Willott et al., Experimental Neurology, vol. 99, No. 3, pp. 615-621, 1988.

McCracken et al., "Probiotics and the Immune System," Position Paper, www.ISAPP.net/docs/immune.pdf, 1999.

McGee et al. "A Gyncrgistic Relationship Between TNF-x, IL-1B and TGF-B1 on ILL-6 Secretion by the IEC-6 Intestinal Epithelial Cell Lines," Immunology, vol. 86, pp. 6-11,1995.

Arai et al., "Cytokines: Coordinates of Immune and Inflammatory Responses," Annu. Rev. Biochem. vol. 90, No. 59, pp. 783-836, 1990.

Anand et al., "Cytokines and Inflammatory Bowel Disease," Tropical Gastroenterology, vol. 20, No. 3, pp. 96-106, 1999.

Andus et al., "Imbalance of the Interleukin 1 System in Colonic Mucosa—Association with Intestinal Inflammation and Interleukin 1 Receptor Agonist Genotype 2," Gut, vol. 41, pp. 651-657, 1997.

Aranda et al., "Analysis of Intestinal Lymphocytes in Mouse Colitis Medicated by Transfer of CD4+, CD45RB high T Cells to SCID Recipients," Journal of Immunology, pp. 3464-3473, 1997.

Barbara G., et al., A Role for Inflammation in Irritable Bowel Syndrome, Gut, vol. 51, Supp. 1, pp. i41-i44, 2002.

Binder, Henry J., M.D., "Genes, Bacteria and T Cells: Ingredients for Inflammatory Bowel Disease," Selected Summaries, Gastroenterology, vol. 115, No. 6, pp. 1695-1700, 1998.

Bodmeier R., "Capsule With Controlled Active Ingredient Release Comprises Active Ingredient-Containing Filling, Capsule Shell, Swelling Agent and Water-Insoluble Layer," 2001-092623/11, A96 B07, BODM, May 18, 1999.

Bouhnik et al., "Effects of *Bifidobacterium* SP Fermented Milk Ingested with or without Inulin on Colonic Bifidobacteria and Enczymatic Activities in Healthy Humans," European Journal of Clinical Nutrition, vol. 50, pp. 269-273, 1996.

Brandtzaeg et al., "Immunopathology of Human Inflammatory Bowel Disease," Springer Seminars in Immunopathology, vol. 18, pp. 555-589, 1997.

Chadwick et al., "Activation of the Mucosal Immune System in Irritable Bowel Syndrome," Gastroenterology, vol. 122, pp. 1778-1783, 2002.

Charteris et al., "Antiobiotic Sysceptibility of Potentially Probiotic *Bifidobacterium* Isolates From the Human Gastrointestinal Tract," Letters in Applied Microbiology, vol. 26, pp. 333-337, 1998.

Charteris et al., "Development and application of an In Vitro Methodologoy to Determine the Transit Tolerance of Potentially Probiotic *Lactobacillus* and *Bifidobacterium* Species in the Upper Human Gastrointestinal Tract," Journal of Applied Microbiology, vol. 84, pp. 759-768, 1998.

Charteris et al., "Selective Detection, Enumeration and Identification of Potentially Probiotic *Lactobacillus* and *Bifidobacterium* Species in Mixed Bacterial Populations," International Journal of Food Microbiology, vol. 35, pp. 1-27, 1997.

Charteris et al., "Effect of Conjugated Bile Salts on Antibiotic Susceptibility of Bile Salt-Tolerant *Lactobacillus* and *Bifidobacterium* Isolates," Journal of Food Protection, vol. 63, No. 10, pp. 1369-1376, 2000.

Cicco et al., "Inducible Production of Interluekin-6 by Human Polymorphonuclear Neutrophils: Role of Granulocyte-Macrophage Cology-Stiumulating Factor and Tumor Necrosis Factor-Alpha," Blood, vol. 75, No. 10, pp. 2049-2052, May 15, 1990.

Donnelly et al., "Differential Regulation of Il-1 Production in Human Monocytes by IFN-y and IL-4," The Journal of Immunology, vol. 145, No. 2, pp. 569-575, Jul. 15, 1990.

Dunne et al., "Probiotics: From Myth to Reality. Demonstration of Functionality in Animal Models of Disease and in Human Clinical Trials," Antonie Van Leeuwenhoek, vol. 76, July-November, No. 104, pp. 279-292, 1999, Abstract.

McCarthy et al., "Double Blind, Placebo Controlled Trial of Two Probiotic Strains in Interleukin 10 Knockout Mice and Mechanistic Link with Cytokine Balance," GUT, vol. 52, pp. 975-980, 2003.

Hommes et al., "Anti- and Proinflarnmatory Cytokines in the Pathogenesis of Tissue Damage in Crohn's Disease," Lippincott Williams and Wilkins, pp. 1363-1950, 2000.

McKay et al., "Review article: In Vitro Models in Inflammatory Bowel Disease," Alignment Pharmacol. Ther., vol. 11, (suppl. 3) pp. 70-80, 1997.

(56) References Cited

OTHER PUBLICATIONS

Lakatos L., "Immunology of Inflammatory Bowel Diseases," Acta Physiological Hungarica., vol. 87 No. 4, pp. 355-372, 2000.
Monteleone et al., "Manipulation of Cytokines in the Management of Patients With Inflammatory Bowel Disease," Ann Med., vol. 32, No. 8, pp. 552-560, 2000.
Marteau et al., "Potential of Using Lactic Acid Bacteria for Therapy and Immunomodulation in Man," FEMS Microbiologoy Reviews, vol. 12, pp. 207-220, 1993.
Medaglini et al., "Mucosal and Systemic Immune Responses to a Recombinant Protein Expressed on the Surface of the Oral Commensal Bacterium *Streptococcus gordonii* after oral colonization," Proc. Natl. Acad. Sci. USA, Medical Sciences, vol. 92, pp. 6868-6872, Jul. 1992.
McBrearty et al., "Probiotic Bifidobacteria and Their Identification Using Molecular Genetic Techniques," Teagasc, Dairy Products Research Centre, Moorepark, Fermoy, Co. Cork, Ireland Department of Microbiology, University College Cork, Ireland, pp. 97-107, 2000.
McGee et al., "A Synergistic Relationship Between TNF-x, IL-1B, and TGF-Bl on IL-6 Secretion by the IEC-6 Intestinal Epithelial Cell Line," Immunology, vol. 86, pp. 6-11, 1995.
Chevalier et al., "Detection of *Bifidobacterium* Species by Enzymatic Methods," Journal of Applied Basteriology, vol. 68, pp. 619-624, 1990.
Gibson et al., "Dietary Modulation of the Human Gut Microflora Using Prebiotics," Journal of Nutrition, vol. 80m Supp. 2, pp. S209-S212, 1998.
Chauviere et al., "Adhension of Human *Lactobacillus acidophilus* Strain LB to Human Enterocyte-like Caco-2 Cells," Journal of General Microbiology, vol. 138, pp. 1689-1696, 1992.
Aga, Abstracts, Gastroenterology, vol. 116, No. 4, Apr. 1999.
Hildesheim et al., "Simultaneous Measurement of Several Cytokines Using Small Volumes of Biospecimens," Cancer Epidemiology, Biomarkers & Prevention, vol. IKI, pp. 1477-1484, Nov. 2002.
Iwasaki et al., "Unique Functions of CD11b+, CD8a+ and Double-Negative Peyer's Patch Dendritic Cells," The American Association of Immunologists, Journal of Immunology, pp. 4884-4890, 2001.
Tomomatsu, Hideo "Health Effects of Oligosaccharides," Food Technology, vol. 48, pp. 61-65, 1994.
Lab Prod. Ethiques Ethypharm., "Coated Microgranules Containing a Gastric Protoon Pump Inhibitor with Two Hydrophobic Materials, Free From Alkali and Any Ionic Surfactant," Derwent Publications Ltd., Ethi., May 21, 1999.
Sener et al. "Environmental modulation of D-fructose insulinotropic action" Acta Diabetol (1998) 35: pp. 74-76.
Zhang et al. "Dissimilar effects of D-mannoheptulose on the phosphorylation of a-versus β-D-glucose by either hexokinase or glucokinase" International Journal of Molecular Medicine 14: pp. 107-112, 2004.
Pelicano et al. "Glycolysis inhibition for anticancer treatment" Oncogene (2006) 25, pp. 4633-4646.
Frech et al. "The Utility of Nutraceuticals in the Treatment of Osteoarthritis" Current Rheumatology Reports 2007, 9: pp. 25-30.
Conde et al. "OeMST2 Encodes a Monosaccharide Transporter Expressed throughout Olive Fruit Maturation" Plant Cell Physiol 48(9): pp. 1299-1308 (2007).
Wamelink et al. "Detection of transaldolase deficiency by quantification of novel seven-carbon chain carbohydrate biomarkers in urine" J Inherit Metab Dis (2007) 30: pp. 735-742.
Katzmarzyk "The metabolic syndrome: an introduction" Appl. Physiol. Nutr. Metab. 32: pp. 1-3 (2007).
Barge "Avocados May Help Prevent Oral Cancer, OSU Study Shows" Journal of Dental Hygiene, vol. 82, No. 2, Apr. 2008, 3 pages.
Ernst "Avacado-soybean unsaponifiables (ASU) for osteoarthritis—a systemic review" Clin Rheumatol (2003) 22: pp. 285-288.
Gondwe "Effects of Oersea Americana Mill (Lauraceae) ["Avacado"] Ethanolic Leaf Extract on Blood Glucose and Kidney Function in Streptozotocin-Induced Diabetic Rats and on Kidney Cell Lines of the Proximal (LLC-PK1) and Distal Tubules (MDBK)" Methods Find Exp Clin Pharacol 2008, 30(1) pp. 25-35.
Rezek et al. "Insulin dependence of paradoxical overeating: effect of mannoheptulose, somatostatin, and cycloheximide" 1979 the American Physiological Society E205-E211.
Walker-Bone "'Natural Remedies' in the Treatment of Osteoarthritis" Drugs Aging 2003: 20(7) pp. 517-526.
Ojewole et al. "Cardiovascular effects of Persea Americana Mill (Lauraceae) (avocado) aqueous leaf extract in experimental animals" Cardiovasc J Afr 2007; 18: pp. 69-76.
Winnock et al. "Correlation between GABA release from rat islet β-cells and their metabolic state" Am J Physiol Endocrinol Metab 282: E937-E942 2002. 7 pages.
Brown et al. "Glucose Phosphorylation is Essential for the Turnover of Neutral Lipid and the Second Stage Assembly of Triacylglycerol-Rich ApoB-Cantaining Lipoproteins in Primary Hepatocyte Cultures" American Heart Association, Inc. 1999, pp. 321-329.
Langhans et al. "Changes in Food intake and Meal Patterens following Injection of D-Mannoheptulose in Rats" Behavioral and Neural Biology 38, pp. 269-286 (1983).
Ashcroft et al. "Glucose Metabolism in Mouse Pancreatic Islets" Biochem J. (1970) 118, pp. 143-154.
Johnson et al. "Glucose-Dependent Modulation of Insulin Secretion and Intracellular Calcium Ions by GKA50, a Glucokinase Activator" Diabetes vol. 56, Jun. 2007 pp. 1694-1702.
Brai et al. "Hypoglycemic and Hypocholesterolemic potential of Persea Americana Leaf Extracts" J Med Food 2007 pp. 356-360.
Klain et al. "Mannoheptulose and Fatty Acid Synthesis in the Rat" The journal of Nutrition pp. 473-477, 1974.
Wood et al. "Evidence for Insulin Involvement in Arginine- and Glucose-Induced Hypercalciuria in Rat" J Nutr. 113: pp. 1561-1567, 1983.
Scruel et al. "Interference of D-mannoheptulose with D-glucose phosphorylation, metabolism and functional effects: Comparison between liver, parotid cells and pancreatic islets" Molecular and Cellular Biochemestry 187: pp. 113-120, 1998.
Chan et al. "Ultra structural and secretory heterogeneity of fa/fa (Zucker) rat islets" Molecular and Cellular Endcrinology 136 (1998) pp. 119-129.
Gallagher et al. "The effects of traditional antidiabetic plants on in vitro glucose diffusion" Nutrition Research 23 (2003) pp. 413-424.
Au et al. "Avacado soybean unsaponifiables (ASU) suppress TNF-a, IL-lb, cox-2, iNOS gene expression, and prostaglandin E2 and nitric oxide production in articular chondrocytes and monocyte/macrophages" OsteoArthritis and Carthage (2007) 15, 18 pages.
Henrotin et al. "Pharmaceutical and nutraceutical management of canine osteoarthritis: Present and future perspectives" The veterinary Journal 170 (2005) pp. 113-123.
Issekutz B. et al. Effect of mannaheptulise on Glucose Kinetics in Normal and Glucocorticoid Treated Dogs. Life Sciences 15(4) 635-643, 1974.
Kibenge M. et al Identification of Biochemical Defects in Pancreatic Islets of fa/fa Rats. Obesity Research 3(2) 171-178, Mar. 1995.
Board M. et al High Km Glucose Phosphorylating (Gluokinase) Activities in a Range of Tumor Cell Lines and Inhibition of Rates of Tumor Growth by the Specific Enzyme Inhibitor Mannoheptulose. Cancer Research vol. 55, pp. 3278-3285, Aug. 1995.
Maklashina E. et al Is Defective Electron Transport at the Hub of Aging. Aging Cell vol. 3, 21-27, 2004.
Publication download from http://wikipedia.org/wiki/Noni on May 4, 2009, 9 pages.
Mermelstein, Food Technology, vol. 51(10), p. 96, 1997.
Archived pages from http://web.archive.org for http://mcdtechnologies.com dated Jan. 2003.
Archived pages from http://web.archive.org for http://mcdtechnologies.com dated 2/003.
Nordal et al. J. Am. Chem. Soc., 1954, vol. 76(20), pp. 5054-5055.
Breeders Choice AvoDERM product brochures http://www.breeders-choice.com/about/brochures.htm Information accessed Feb. 3, 2009.
Blue Buffalo Life Protection Formula_package.pdf http://www.bluebuff.com/products/dogs/lp-adult-chick.shtml Information accessed Feb. 3, 2009.

(56) References Cited

OTHER PUBLICATIONS

Natures Logic Natural Chicken Meal_package.pdf http://www.natureslogic.com/products/dp_dry_chi.html Information accessed Feb. 3, 2009.

Natures Logic_Natural Chicken Dinner Fare FROZEN_package.pdf http://www.natureslogic.com/products/dp_rf_chi.html Information accessed Feb. 3, 2009.

Shimada, N., "Signifiance of 1, 5-Anhrdro-D-Glucitol in Diabetes Mellitus Management," Sangyo Igaku, 1994, 36($^3$) pp. 448-449. (As provided by the USPTO in Office Action dated Sep. 9, 2004, for U.S. Appl. No. 09/950,052.).

Robey et al. Akt, hexokinase, mTOR: Targeting cellular energy metabolism for cancer therapy, Drug Discovery Today: Disease Mechanisms, vol. 2 No. 2 2005; pp. 239-246.

Kappler-Tanudyaya et al. Combination of biotransformation and chromatography for the isolation and purification of mannoheptulose; Biotechnol. J. 2007, 2; pp. 692-699.

Simon et al. Insulin and Proinsulin Secretion and Action; Israel J. Med. Sci. vol. 8, No. 6, Jun. 1972.

Nordal et al. Isolation of mannoheptulose and identification of its phosphate in avocado leaves, Meddelelser fra Norsk Farmaceutisk Selskap (1955), 17, 207-213.

Aga, Abstracts, Gastroenterology, vol. 116, No. 4.

Anand et al., "Cytokincs and Inflammatory Bowel Disease," Tropical Gastroenterology, 1999, 20 (3), pp. 97-106.

Andus et al., "Imbalance of the Interleukin 1 System in Colonic Mucosa—Association With Intestinal Inflammation and Interleukin 1 Receptor Agonist Genotype 2," Gut, vol. 41, 1997, pp. 651-657, p. 654, col. 2-p. 655, col. 1, fig. 2D.

Arai et al., "Cytokines: Coordinates of Immune and Inflammatory Responses," Annu. Rev. Biochem. 90, 59: 783-836.

Aranda et al., "Analysis of Intestinal Lymphocytes in Mouse Colitis Medicated by Transfer of CD4+, CD45RB high T Cells to SCID Recipients," 1997, The American Assoc. of Immunologists.

Barbara G., et al., A Role for Inflammation in Irritable Bowel Syndrome, Gut, 51, pp. i41-i44.

Binder, Henry J., M.D., "Genes, Bacteria and T Cells: Ingredients for Inflammatory Bowel Disease," Selected Summaries, Gastroenterology, 1998, 115, pp. 1695-1700, vol. 115, No. 6.

Bodmeier R., "Capsule With Controlled Active Ingredient Release Comprises Active Ingredient-Containing Filling, Capsule Shell, Swelling Agent and Water-Insoluble Layer," BODM, May 18, 1999.

Bouhnik et al., "Effects of Bifidobacterium SP Fermented Milk Ingested with or without Inulin on Colonic Bifidobacteria and Enezymatic Activities in Healthy Humans," European Journal of Clinical Nutrition, 1996, 50, pp. 269-273.

Brandtzaeg et al., "Immunopathology of Human Inflammatory Bowel Disease," Springer Seminars in Immunopathology, 1997, 18, pp. 555-589.

Chadwick et al., "Activation of the Mucosal Immune System in Irritable Bowel Syndrome," Gastroenterology, 2002, 122, pp. 1778-1783.

Charteris et al., "Antiobiotic Sysceptibility of Potentially Probiotic Bifidobacterium Isolates From the Human Gastrointestinal Tract," Letters in Applied Microbiology, 1998, vol. 26, pp. 333-337.

Charteris et al., "Development and application of an in Vitro Methodologoy to Determine the Transit Tolerance of Potentially Probiotic Lactobacillus and Bifidobacterium Species in the Upper Human Gastrointestinal Tract," Journal of Applied Microbiology, 1998, vol. 84, pp. 759-768.

Charteris et al., "Selective Detection, Enumeration and Identification of Potentially Probiotic Lactobacillus and Bifidobacterium Species in Mixed Bacterial Populations," International Journal of Food Microbiology 35, 1997, pp. 1-27.

Charteris et al., "Effect of Conjugated Bile Salts on Antibiotic Susceptibility of Bile Salt-Tolerant Lactobacillus and Bifidobacterium Isolates," Journal of Food Protection, vol. 63, No. 10, 2000, pp. 1369-1376.

Chauviere et al., "Adhension of Human Lactobacillus acidophilus Strain LB to Human Enterocyte-like Caco-2 Cells," Journal of General Microbiology, 1992, vol. 138, pp. 1689-1696.

Chevalier et al., "Detection of Bifidobacterium Species by Enzymatic Methods," Journal of Applied Basteriology, 1990, vol. 68, pp. 619-624.

Cicco et al., "Inducible Production of Interluekin-6 by Human Polymorphonuclear Neutrophils: Role of Granulocyte-Macrophage Cology-Stiumulating Factor and Tumor Necrosis Factor-Alpha," 1990, The American Society of Hematology, Blood, vol. 75, No. 10, May 15, 1990, pp. 2049-2052.

Collins et al., "Selection of Probiotic Strains for Human Applications," In. Dairy Journal 8, 1998, 487-490.

Donnelly et al., "Differential Regulation of II-1 Production in Human Monocytes by IFN-y and IL-4," The Journal of Immunology, vol. 145, pp. 569-575, No. 2, Jul. 15, 1990.

Dorland's Pocket Medical Dictionary ($24^{th}$ ed.), W. B. Saunders Co., p. 15, 1989.

Dunne et al., "Probiotics: From Myth to Reality. Demonstration of Functionality in Animal Models of Disease and in Human Clinical Trials."

Gasche et al., "IL-10 Secretion and Sensitivity in Normal Human Intestine and Inflammatory Bowel Disease," Journal of Clinical Immunology, vol. 20, No. 5, 2000.

Gibson et al., "Dietary Modulation of the Human Gut Microflora Using Prebiotics," Journal of Nutrition, 1998, 80, suppl. 2 S209-S212.

Groux et al., "Regulatory T Cells and Inflammatory Bowel Disease," Viewpoint Immunologoy Today, Oct. 1999.

Hideo Tomomatsu, "Health Effects of Oligosaccharides," 1994, Food Technology 48, pp. 61-65.

Hildesheim et al., "Simultaneous Measurement of Several Cytokines Using Small Volumes of Biospecimens," Cancer Epidemiology, Biomarkers & Prevention, vol. IKI, pp. 1477-1484, Nov. 2002, abstract.

Hommes et al., "Anti- and Proinflammatory Cytokines in the Pathogenesis of Tissue Damage in Crohn's Disease," 2000 Lippincott Williams and Wilkins, pp. 1363-1950.

Iwasaki et al., "Unique Functions of CD11b+, CD8a+ and Double-Negative Peyer's Patch Dendritic Cells," 2001, The American Association of Immunologists.

Kyoto Yakuhin KK, "Sustains-Release Formulation Which Floats in Stomach-Comprises Core of Fats and Oils, Coated with Drug Containing Layer of e.g. Agar," KYOT, Jul. 10, 1987.

Lab Prod. Ethiques Ethypharm., "Coated Microgranules Containing A Gastric Protoon Pump Inhibitor witih Two Hydrophobic Materials, Free From Alkali and Any Ionic Surfactant," Derwent Publications Ltd., Ethi. May 21, 1999.

Lakatos L., "Immunology of Inflammatory Bowel Diseases," Acta Physiologica Hungarica., vol. 87 (4), pp. 355-372, 2000.

Marteau et al., "Potential of Using Lactic Acid Bacteria for Therapy and Immunomodulation in Man," FEMS Microbiologoy Reviews 12, 1993, pp. 207-220.

McBrearty et al., "Probiotic Bifidobacteria and Their Identification Using Molecular Genetic Techniques," Teagasc, Dairy Products Research Centre, Moorepark, Fermoy, Co. Cork, Ireland Department of Microbiology, University College Cork, Ireland.

McCarthy et al., "Double Blind, Placebo Controlled Trial of Two Probiotic Strains in Interleukin 10 Knockout Mice and Mechanistic Link with Cytokine Balance," Gastroenterology, vol. 122, nr. 4, suppl. 1, pp. A389-A390, DDW Meeting Abstract, Nr. T962.

McCracken et al., "Probiotics and the Immune System."

McGee et al., "A Synergistic Relationship Between TNF-x, IL-1B, and TGF-B1 on IL-6 Secretion by the IEC-6 Intestinal Epithelial Cell Line," Immunology, 1995, 86, pp. 6-11.

McKay et al., "Review article: In Vitro Models in Inflammatory Bowel Disease," Aliment Pharmacol. Ther., 1997, 11 (suppl. 3) pp. 70-80.

Medaglini et al., "Mucosal and Systemic Immune Responses to a Recombinant Protein Expressed on the Surface of the Oral Commensal Bacterium Streptococcus gordonii after oral colonization," Proc. Natl. Acad. Sci. USA, vol. 92, pp. 6868-6872, Jul. 1992 Medical Sciences.

(56) References Cited

OTHER PUBLICATIONS

Monteleone et al., "Manipulation of Cytokines in the Management of Patients With Inflammatory Bowel Disease," Ann Med., Nov. 2000; 32(8), pp. 552-560.

Morishita Jintan KK, "Capsule Preparation for Enteral Administration of Unsaturated Fatty Acids (Jpn)," Derwent Publications Ltd., MORI, Oct. 30, 1997.

Morishita Jintan KK, "Yogurt for Supply Physiologically Important Intestinal Bacteria—Contains Bacteria Contained in Capsule Having Inner Layer Made of Digestible Substance and Outer Layer Dissolving in Intestine," MORI, Mar. 10, 1995.

O'Callaghan et al., "Differential Cytokine Response of Cells Derived from Different Lymphoid Compartments to Commensal and Pathogenic Bacteria.".

O'Halloran et al., "Adhesion of Potential Probiotic Bacteria to Human Epithelial Cell Lines," Departments of Microbiologoy and Medicine, University College, Mercy Hospital Cork, Ireland, Dept. of Surgery, Mercy Hospital Cork Ireland.

O'Mahony et al., Probiotic Bacteria and Pathogenic Bacteria Elicit Differential Cytokine Responses From Dendritic Cells, XP-001097379.

O'Mahony et al., "Probiotic Impact on Microbial Flora, Inflammation and Tumour Development in IL-10 Knockout Mice," Aliment Pharmacol Ther, 2001, 15, pp. 1219-1225.

O'Mahony et al., "Probiotic Bacteria and the Human Immune System," Dept. Microbiology and Medicine, National Food Biotechnology Centre, University College Cork & Dept. Surgery, Mercy Hospital, Cork Ireland.

Panwala et al., "A Novel Model of Inflammatory Bowel Disease: Mice Deficient for the Multiple Drug Resistance Gene, mdrla, Spontaneously Develop Colitis," The American Association of Immunologists, 1998, The Journal of Immunology, 1998, 161, pp. 5733-5744.

Powrie et al., "Inhibition of the 1 Responses Prevents Inflammatory Bowel Disease in Scid Mice Reconstituted with CD45Rbhi CD4+ T Cells," Immunity, vol. 1, pp. 553-562, Oct. 1994.

Rogler et al., "Cytokines in Inflammatory Bowel Disease," World Journal of Surgery, vol. 22, 1998, pp. 382-389, XP002296948—whole document.

Roth et al., Ann. NY Acad Sci. 928, pp. 305-315, 2001.

SS Pharmaceutical KK, Tablets Containing Double-Coated Granules-Obtained by Coating with Insol. Polymer, Enteric Polymer and/or Waxes, Then Further Coating with Water or Acid-Soluble Polymer, SSSE, Aug. 18, 1988.

Scardovi, V. "Irregular Nonsporing Gram-Positive Rods," Genus Bifidobacterium Orla-Jensen, 1924, 472.

Schmitt et al., "The Immunostimulatory Function of IL-12 in T-Helper Cell Development and its Regulation by TGF-B, IFN-y and TL-4," Chem. Immunet Basel Karger, 1997, vol. 68, pp. 70-85.

Shimada, N., "Significance of 1, 5-Anhydro-D-Glucitol in Diabetes Mellitus Management," Sangyo Igaku, 1994, 36(6) pp. 448-449. (As provided by the USPTO in Office Action dated Sep. 9, 2004, for U.S. Appl. No. 09/950,052.).

Snow Brand Milk Products< "Enteric Capsules—Comprising Core Containing Drug etc. and Coating of Hardened Oil of M. Pt. Higher than Body Temp. and Disintegrated by Lipase in Intestine," SNOW, Mar. 31, 1986.

Soudeyns et al., "The Moving Target: Mechanisms of HIV Persistence During Primary Infection," Immunology Today, Oct. 1999.

Stagg et al., "The Dendritic Cell: It's Role in Intestinal Inflammation and Relationship with Gut Bacteria," www. Gutjnl.com.

Stallmach et al., "Induction and Modulation of Gastrointestinal Inflammation," Trends Immunology Today, Oct. 1998, vol. 19, No. 10, pp. 438-441.

Strober et al., "Reciprocal IFN-gamma and TFG-Beta Responses Regulate the Occurrence of Mucosal Inflammation," Immunol. Today, Feb. 18, 1997, (2) pp. 61-64.

Takeda Chemical Ind KK, "Dry Coated Tablet—Comprises Core Tablets Containing Enzyme Prepn. In Enteric Films Within Outer Shell," TAKE May 10, 1982.

Van Damme et al., "The Proportion of Th 1 Cells, Which Prevail in Cut Mucosa, is Decreased in Inflammatory Bowel Syndrome," 2001, Blackwell Science Ltd. Clinical and Experimental Immunology, 125, pp. 383-390.

Vickers et al., "Comparison of Fermentation of Selected Fructooligosaccharides and Other Fiber Substrates by Canine Colonic Microflora," AJVR, vol. 62, No. 4, Apr. 2001.

Voet, Donald and Judith G., Biochemistry, John Wileyl & Sons, Inc. pp. 1044-1045.

Wein et al., "Analyzing a Bioterror Attack on the Food Supply: The Case of Botolinum Toxin in Milk," 2005, The National Academy of Sciences of the USA.

Willott et al., Exp. Neurol. vol. 99(3), pp. 615-621.

Yu "Modulation of Aging Processes by Dietary Restriction".

All Office Actions, U.S. Appl. No. 09/950,052 (now abandoned).
All Office Actions, U.S. Appl. No. 11/313,198 (now abandoned).
All Office Actions, U.S. Appl. No. 12/082,710.
All Office Actions, U.S. Appl. No. 11/313,199 (now abandoned).

* cited by examiner

METHOD OF MAINTAINING AND/OR ATTENUATING A DECLINE IN QUALITY OF LIFE

CROSS-REFERENCE TO RELATED APPLICATIONS

This application is a continuation-in-part of application Ser. No. 11/313,199, filed Dec. 20, 2005, now abandoned, which is a continuation-in-part of application Ser. No. 09/950,052, filed Sep. 12, 2001 now abandoned, which is a continuation-in-part of application Ser. No. 08/889,877, filed Jul. 8, 1997 now abandoned.

FIELD OF THE INVENTION

In an embodiment, the present invention relates to the use of glucose anti-metabolites to alter utilization of glucose or other carbohydrate sources and to mimic metabolic effects of caloric restriction for the purpose of maintaining and/or attenuating a decline in the health, functional activity and/or biomarkers of longevity in a mammal. In an embodiment, the present invention relates to the use of glucose anti-metabolites to mimic effects of caloric restriction for the purpose of maintaining and/or attenuating a decline in the quality of life of a mammal. In an embodiment, the present invention is directed to compositions comprising a selected carbohydrate component, or extract of plant material selected from avocado, alfalfa, fig, primrose, and mixtures thereof.

BACKGROUND OF THE INVENTION

Biological theories have correctly predicted the finding that a restriction of caloric intake by food deprivation slows down certain undesirable cellular processes in laboratory animals, many associated with aging and age-related diseases.

In particular, caloric restriction has been shown to consistently extend the life span, delay onset and slow tumor progression, and retard physiologic aging in many systems. Indeed, research spanning more than sixty years has shown that caloric restriction is a nutritional intervention that consistently extends longevity in animals. See Weindruch and Walford, "The Retardation of Aging and Disease by Dietary Restriction," Springfield, Ill.: Charles C. Thomas (1988); Yu, "Modulation of Aging Processes by Dietary Restriction," Boca Raton: CRC Press (1994); and Fishbein, "Biological Effects of Dietary Restriction," Springer, New York (1991). These effects of caloric restriction on life span and tumorigenesis have been reported numerous times since the early studies of McKay. See McKay et al., "The Effect of Retarded Growth Upon the Length of Lifespan and Upon Ultimate Body Size," J. Nutr., Vol. 10, pp. 63-79 (1935). Indeed, over the past two decades, a resurgence of interest in caloric restriction in gerontology has led to the general acceptance that this dietary manipulation slows physiologic aging in many systems. See Weindruch and Walford, "The Retardation of Aging and Disease by Dietary Restriction," Springfield, Ill.: Charles C. Thomas (1988); Yu, "Modulation of Aging Processes by Dietary Restriction," Boca Raton: CRC Press (1994); and Fishbein, "Biological Effects of Dietary Restriction," Springer, New York (1991) and Masoro, E. J. "Overview of Caloric Restriction and Aging," Mech. Aging Dev., Vol. 126, pp 913-922 (2005).

Reductions in fasting glucose and insulin levels and improvements in insulin sensitivity are readily measured biomarkers of caloric restriction. Calorically restricted rodents exhibit lower fasting glucose and insulin levels, and the peak glucose and insulin levels reached during a glucose challenge are reduced in those on caloric restriction. See Kalant et al., "Effect of Diet Restriction on Glucose Metabolism and Insulin Responsiveness and Aging Rats," Mech. Aging Dev., Vol. 46, pp. 89-104 (1988). It is also known that hyperinsulinemia is a risk factor associated with several such disease processes, including heart disease and diabetes (Balkau and Eschwege, Diabetes Obes. Metab. 1 (Suppl. 1): S23-31, 1999). Reduced insulin levels and body temperature are two of the most reliable indicators of this altered metabolic profile (Masoro et al., J. Gerontol. Biol. Sci. 47:B202-B208, 1992); Koizumi et al., J. Nutr. 117: 361-367, 1987; Lane et al., Proc. Nat. Acad. Sci. 93:4154-4164, 1996).

Glucose anti-metabolites such as 2-deoxy-D-glucose are compounds related to glucose. However, due to structural differences from glucose such compounds block or inhibit certain aspects of carbohydrate metabolism and may therefore mimic the effects of caloric restriction (Rezek et al., J. Nutr. 106:143-157, 1972). These anti-metabolites exert a number of physiological effects, including reduction of body weight, decrease in plasma insulin levels, reduction of body temperature, retardation of tumor formation and growth, and elevation of circulating glucocorticoid hormone concentrations. (For a review see Roth et al., Ann. NY Acad. Sci. 928:305-315, 2001). These physiological effects result from inhibition of carbohydrate metabolism.

As such, use of glucose anti-metabolites as components for maintaining and/or attenuating a decline in the health, functional activity and/or biomarkers of longevity in mammals, for example through decreasing abnormalities of glucose metabolism, would be beneficial. It would be beneficial to provide glucose anti-metabolites having physiological effects on the cellular processes associated with aging and age-related diseases. It would be beneficial to provide glucose anti-metabolites having physiological effects on the cellular processes associated with aging and age-related diseases wherein the physiological effects maintain and/or attenuate a decline in the quality of life of a mammal. It would be beneficial to provide components for maintaining and/or attenuating a decline in the quality of life of a mammal, such as, but not limited to, maintaining and/or attenuating a decline in the whole body composition and maintaining and/or attenuating a decline in the functional mobility of a mammal. It would be beneficial to provide compositions comprising such glucose anti-metabolite components. It would be beneficial to provide compositions comprising glucose anti-metabolite components that may maintain and/or attenuate a decline in the quality of life of a mammal.

SUMMARY OF THE INVENTION

A method of maintaining and/or attenuating a decline in the quality of life of a mammal, the method comprising the step of administering to the mammal a composition comprising an effective amount of mannoheptulose wherein the effective amount of mannoheptulose provides a dosage to the mammal on a daily basis from about 0.001 gram per kilogram of body weight of the mammal to about 1 gram per kilogram of body weight of the mammal, wherein the maintaining and/or attenuating a decline in the quality of life of the mammal is selected from the group consisting of maintaining and/or attenuating a decline in whole body composition, maintaining and/or attenuating a decline in functional mobility, and combinations thereof.

A method of maintaining and/or attenuating a decline in whole body composition in a mammal, the method comprising the step of administering to the mammal a composition comprising an effective amount of mannoheptulose wherein the effective amount of mannoheptulose provides a dosage to the mammal from about 0.001 gram per kilogram of body weight of the mammal to about 1 gram per kilogram of body weight of the mammal per day.

A method of maintaining and/or attenuating a decline in musculoskeletal health in a mammal, the method comprising the step of administering to the mammal a composition comprising an effective amount of mannoheptulose wherein the effective amount of mannoheptulose provides a dosage to the mammal from about 0.001 gram per kilogram of body weight of the mammal to about 1 gram per kilogram of body weight of the mammal per day.

A method of maintaining and/or attenuating a decline in the functional mobility of a mammal, the method comprising the step of administering to the mammal a composition comprising an effective amount of mannoheptulose wherein the effective amount of mannoheptulose provides a dosage to the mammal from about 0.001 gram per kilogram of body weight of the mammal to about 1 gram per kilogram of body weight of the mammal per day.

DETAILED DESCRIPTION OF THE INVENTION

Figure 1:
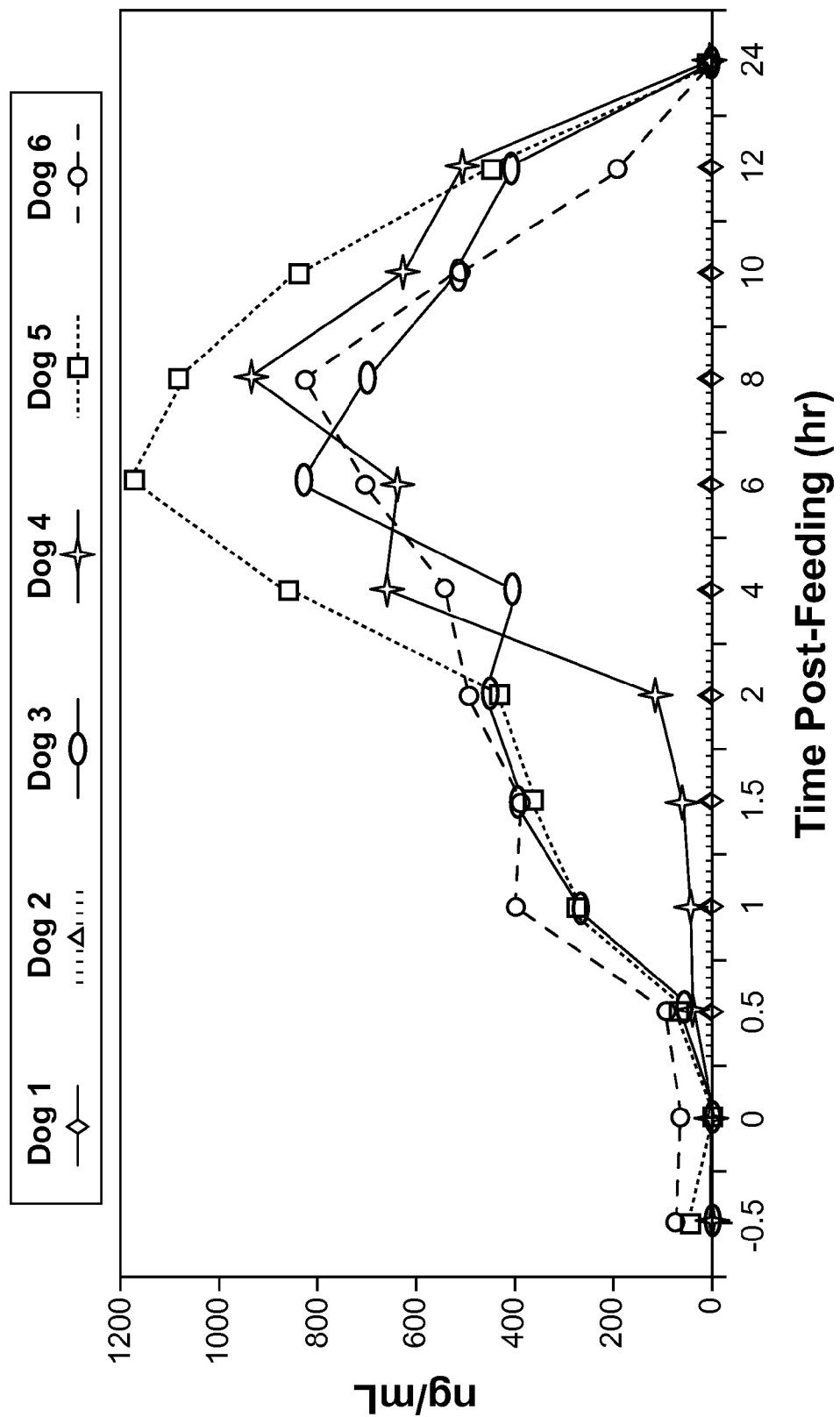
FIG. 1 is a graphical presentation of serial concentrations of plasma mannoheptulose in adult Labrador Retrievers fed a single meal of a nutritionally balanced composition containing mannoheptulose at a dose of 0, 1 or 2 mg/kg of the body weight of the dog.

Various documents including, for example, publications and patents, are recited throughout this disclosure. All such documents are hereby incorporated by reference. The citation of any given document is not to be construed as an admission that it is prior art with respect to the present invention.

All percentages and ratios are calculated by weight unless otherwise indicated. All percentages and ratios are calculated based on the total composition unless otherwise indicated.

Referenced herein are trade names for components including various ingredients utilized in the present invention. The inventors herein do not intend to be limited by materials under a certain trade name. Equivalent materials (e.g., those obtained from a different source under a different name or reference number) to those referenced by trade name may be substituted and utilized in the descriptions herein.

In the description of the invention various embodiments or individual features are disclosed. As will be apparent to the ordinarily skilled practitioner, all combinations of such embodiments and features are possible and can result in preferred executions of the present invention.

The compositions herein may comprise, consist essentially of, or consist of any of the features or embodiments as described herein.

While various embodiments and individual features of the present invention have been illustrated and described, various other changes and modifications can be made without departing from the spirit and scope of the invention. As will also be apparent, all combinations of the embodiments and features taught in the foregoing disclosure are possible and can result in preferred executions of the invention.

All oral doses of the invention are calculated per kilogram of body weight of the mammal unless otherwise indicated.

The present invention is directed to compositions comprising a glucose anti-metabolite component selected from the group consisting of 2-deoxy-D-glucose; 5-thio-D-glucose; 3-O-methylglucose; 1,5-anhydro-D-glucitol; 2,5-anhydro-D-glucitol; 2,5-anhydro-D-mannitol; mannoheptulose; and mixtures thereof. Without intending to be limited by theory, it is believed that these components are glucose anti-metabolites. See e.g., U.S. patent application Publication No. 2002/0035701. In another embodiment, the components may be present in the recited compositions by virtue of a component of plant matter such as avocado, or other enriched source of mannoheptulose such as alfalfa, fig, primrose and the like. The present invention is also directed to the use of such compositions for maintaining and/or attenuating a decline in the quality of life of a mammal such as a companion animal. Maintaining and/or attenuating a decline in the quality of life of a mammal includes, but is not limited to, maintaining and/or attenuating a decline in the whole body composition and maintaining and/or attenuating a decline in the functional mobility of a mammal. Maintaining and/or attenuating a decline in the whole body composition of a mammal is maintaining and/or attenuating a decline in the musculoskeletal health of the mammal. Maintaining and/or attenuating a decline in the musculoskeletal health of a mammal is maintaining and/or attenuating a decline in the muscle health and/or skeletal health of the mammal. Maintaining and/or attenuating a decline in the muscle health of a mammal is the maintenance and/or the attenuation of a decline in the lean body mass and/or the muscle strength of the mammal. Maintaining and/or attenuating a decline in the skeletal health of a mammal is the maintenance and/or the attenuation of a decline in the bone mineral density and/or the bone mineral content of the mammal. Maintaining and/or attenuating a decline in the functional mobility of a mammal is maintaining and/or attenuating a decline in the activities of daily living of the mammal. Maintaining and/or attenuating a decline in the activities of daily living is maintaining and/or attenuating a decline in activities such as, but not limited to, playing, walking, climbing, jumping, and running. For example, maintaining and/or attenuating a decline in a jumping activity of a mammal is the maintenance and/or the attenuation of a decline in the ability to jump over obstacles and/or onto surfaces.

The present invention relates to the use of glucose anti-metabolite components to alter utilization of glucose or other carbohydrate sources and to mimic metabolic effects of caloric restriction. Without intending to be limited by theory, the present use of glucose anti-metabolite components to alter glucose metabolism serves to lower the metabolic rate through inhibition of glucose as an energy source on the cellular level. Judicious use of components that block the normal metabolism of cellular glucose can result in changes in physiological function that are similar to those arising from caloric restriction. Caloric restriction has been consistently shown to extend longevity in animals. See Weindruch and Walford, "The Retardation of Aging and Disease by Dietary Restriction," Springfield, Ill.: Charles C. Thomas (1988); Yu, "Modulation of Aging Processes by Dietary Restriction," Boca Raton: CRC Press (1994); and Fishbein, "Biological Effects of Dietary Restriction," Springer, New York (1991).

In one embodiment herein, the invention relates to a method of maintaining and/or attenuating a decline in the health, functional activity, and/or biomarkers of longevity in a mammal, the method comprising administration of a composition comprising a glucose anti-metabolite component to the mammal. In another embodiment, the invention relates to a method of maintaining and/or attenuating a decline in the health, functional activity, and/or biomarkers of longevity in a mammal, the method comprising administration of a composition comprising avocado extract, wherein the avocado extract comprises mannoheptulose. In another embodiment, the invention relates to a method of maintaining and/or attenuating a decline in the health, functional activity, and/or biomarkers of longevity in a mammal, the method comprising administration of a composition comprising avocado meal, wherein the avocado meal comprises mannoheptulose. In yet another embodiment, the invention relates to a method of maintaining and/or attenuating a decline in the health, functional activity, and/or biomarkers of longevity in a mammal, the method comprising administration of a composition comprising mannoheptulose. As used herein, "maintaining and/or attenuating a decline in the health, functional activity, and biomarkers of longevity," with reference to a mammal, includes both qualitative and quantitative measures, such as, for example, prolonging the life span of the mammal, retarding the physiological aging process, reducing incidence of disease, maintaining vitality, and combinations thereof.

In an embodiment, the invention relates to a method of maintaining and/or attenuating a decline in the quality of life of a mammal. The ability of the invention to maintain and/or attenuate a decline in the quality of life may be demonstrated by, but not limited to, maintaining and/or attenuating a decline in the whole body composition, maintaining and/or attenuating a decline in the functional mobility of a mammal and combinations thereof. Maintaining and/or attenuating a decline in the whole body composition of a mammal is maintaining and/or attenuating a decline in the musculoskeletal health of the mammal. Maintaining and/or attenuating a decline in the musculoskeletal health of a mammal is maintaining and/or attenuating a decline in the muscle health and/or skeletal health of the mammal. Maintaining and/or attenuating a decline in the muscle health of a mammal is the maintenance and/or the attenuation of a decline in the lean body mass and/or the muscle strength of the mammal. It is believed that maintenance and/or attenuation of a decline in the lean body mass and/or the muscle strength provides for maintenance and/or attenuation of a decline in muscle functionality such as, but not limited to, power and flexibility. Maintaining and/or attenuating a decline in the skeletal health of a mammal is the maintenance and/or the attenuation of a decline in the bone mineral density and/or the bone mineral content of the mammal. Maintaining and/or attenuating a decline in the functional mobility of a mammal is maintaining and/or attenuating a decline in the activities of daily living of the mammal. Maintaining and/or attenuating a decline in the activities of daily living is maintaining and/or attenuating a decline in activities such as, but not limited to, playing, walking, climbing, jumping, and running. For example, maintaining and/or attenuating a decline in a jumping activity of a mammal is the maintenance and/or the attenuation of a decline in the ability to jump over obstacles and/or onto surfaces. The maintenance and/or attenuation in the decline of body composition and functional mobility allow the mammal to maintain normal levels of voluntary activity despite advancing in age. It is widely accepted by those skilled in the art that mobility, locomotion, movement and/or activity of a mammal requires a healthy and functional musculoskeletal system comprised of bones (skeleton), muscles, and various connective tissues and structures such as cartilage, tendons, ligaments and joints. The invention may maintain and/or attenuate a decline in the measures of locomotion, mobility and/or activity such as, but not limited to, gait, velocity, symmetry, rate of speed, distance traveled, episodes of movement, stamina and endurance. These may result in the maintenance and/or attenuation of a decline in the activities of daily living such as playing, walking, running, jumping, climbing, ascending stairs, descending stairs, standing up, lying down, sleeping and social companionship. Additional benefits may extend to performance mammals engaged in enhanced levels of physical activity and/or sports such as, but not limited to, hunting, sprinting, running, pulling, sledding, retrieving, and agility. The ability to maintain and/or attenuate a decline in these regular and performance activities with advancing age lead to maintenance and/or attenuation of a decline in the quality of life of the mammal. Maintenance and/or attenuation of a decline in the quality of life of a mammal may also include a reduction of body fat, adiposity and/or the control of obesity.

In an embodiment, the invention may maintain and/or attenuate a decline in the immune system of the mammal. Immunity is divided into natural and adaptive immunity. The adaptive branch of the immune system is represented by cellular and humoral immunity and is defined by improved T and B cell responses. These responses are measured by assays such as, but not limited to, tritiated thymidine lymphoproliferative response, altered relative and absolute percent of white blood cell populations as measured by immunofluorescence, Th1 and Th2 cytokine profile changes as measured by commercially available assays, antibody titer production response to vaccine and other antigens, decreased series 2 and 4 eicosanoid and thromboxane production, and increased series 3 and 5 eicosanoid and thromboxane production as measured by commercially available kits. Assessment of the natural or innate branch of the immune system is based on the increased natural killer cell cytotoxic response as measured by Cr-51 release assay.

In an embodiment, the invention may maintain and/or attenuate a decline in the health, functional activity, and/or biomarkers of longevity by reducing the incidence of diseases that include, and are not limited to, obesity, diabetes, thyroid disease, heart disease, metabolic syndrome, Alzheimer's disease, Parkinson's disease, stroke, and cancer. The incidence of these diseases may be reduced by the ability of the invention to manage oxidative stress and inflammation. Maintenance and/or attenuation in the decline of the health of the mammal may be reflected in biomarkers of longevity such as body temperature, insulin, insulin sensitivity Health screening by licensed health care practitioners using standard methods such as physical examinations, blood chemistries, complete blood counts, radiographs, MRI, and CT-scans may show the benefits of the invention on the successful aging and quality of life of the mammal.

Additional quality of life benefits include, but are not limited to, the interaction of the individual with its environment such as behavior, temperament, companionship, social well-being, response to stress, cognition and sensorial abilities including vision, hearing, smell, taste, touch, and satiety. Additional quality of life benefits include, and are not limited to, improved physical appearance such as physique, stature, body condition, skin condition, hair condition, and a more desirable social bond, such as the bond between a human and a companion animal. Additional quality of life benefits may be reflected in various calculated indices of health, wellness, mobility, activity, vitality, frailty, functional living, healthspan, and active longevity.

The ability of the invention to maintain and/or attenuate a decline in the quality of life can be linked to the presence of glucose anti-metabolite components in various biological fluids and tissues following administration of the compositions of the invention to the mammal. These biological fluids include but are not limited to feces, urine, blood, saliva, perspiration, spinal fluid, synovial fluid, milk. Biological tissues include but are not limited to liver, muscle, adipose, kidney, gastrointestinal, buccal, nasal, skin, hair, and/or the cells derived from these tissues.

The mammals treated herein include vertebrates and invertebrates such as for example insects (e.g., the fruit fly) and/or nematodes (e.g., *Caenorbabditis elegans*). Humans and companion animals are advantageously treated herein. As used herein, "companion animal" means a domestic animal. Preferably, "companion animal" means a dog, cat, rabbit, ferret, horse, cow, or the like. More preferably, "companion animal" means a dog or cat.

The glucose anti-metabolite components which are useful herein include 2-deoxy-D-glucose, 5-thio-D-glucose, 3-O-methylglucose, anhydrosugars including 1,5-anhydro-D-glucitol, 2,5-anhydro-D-glucitol, and 2,5-anhydro-D-mannitol, and mannoheptulose. Mannoheptulose is preferred for use herein. Advantageously, mannoheptulose may be present in the recited compositions as a component of plant matter such as an avocado extract, avocado meal or other enriched source of mannoheptulose. Non-limiting examples of enriched sources of mannoheptulose are alfalfa, fig or primrose. The plant matter may include the fruit, seed (or pit), branches, leaves, or any other portion of the relevant plant or combinations thereof.

Avocado (also commonly referred to as alligator pear, aguacate, or palta) contains unusually enriched sources of mannoheptulose, as well as related sugars and other carbohydrates. Avocado is a sub-tropical evergreen tree fruit, growing most successfully in areas of California, Florida, Hawaii, Guatemala, Mexico, the West Indies, South Africa, and Asia.

Species of avocado include, for example, *Persea Americana* and *Persea nubigena*, including all cultivars within these illustrative species. Cultivars may include 'Anaheim,' 'Bacon,' 'Creamhart,' 'Duke,' 'Fuerte,' 'Ganter,' 'Gwen,' 'Hass,' 'Jim,' 'Lula,' 'Lyon,' 'Mexicola Grande,' 'Murrieta Green,' 'Nabal,' 'Pinkerton,' 'Queen,' 'Puebla,' 'Reed,' 'Rincon,' 'Ryan,' 'Spinks,' 'Topa Topa,' 'Whitsell,' 'Wurtz,' and 'Zutano.' The fruit of the avocado is particularly preferred for use herein, which may contain the pit or wherein the pit is removed or at least partially removed. Fruit from *Persea Americana* is particularly preferred for use herein, as well as fruit from cultivars which produce larger fruits (e.g., about 12 ounces or more when the fruit is mature), such as Anaheim, Creamhart, Fuerte, Hass, Lula, Lyon, Murrieta Green, Nabal, Queen, Puebla, Reed, Ryan and Spinks.

Plant matter from alfalfa, fig, or primrose are also reported to provide relatively high levels of mannoheptulose. Alfalfa is also referred to as *Medicago sativa*. Fig, or *Ficus carica* (including Cluster fig or Sycamore fig, for example) may also be used, as well as primrose or *Primula officinalis*.

It has been discovered that particular levels of a component selected from 2-deoxy-D-glucose; 5-thio-D-glucose; 3-O-methylglucose; 1,5-anhydro-D-glucitol; 2,5-anhydro-D-glucitol; 2,5-anhydro-D-mannitol; mannoheptulose; and mixtures thereof, are useful herein. In particular, it has been found that relatively low levels, as well as relatively high doses of the component, while useful, may provide less than optimal efficacy for desired purposes. Dosage will depend upon the glucose anti-metabolite component used and will vary depending upon the size and condition of the mammal to which the glucose anti-metabolite is to be administered. Dosage in the range of 0.0001 or 0.001 grams/kg to about 1 g/kg, per kilogram of body weight of the mammal, is beneficial. Dosage at the lower range would be appropriate when using 2-deoxy-D-glucose in large animals. Higher dosage, particularly of compounds such as 5-thio-D-glucose or mannitol would be readily tolerated. In an embodiment, the dosage of the component provided to a mammal on a daily basis may be from about 1, 2 or 5 mg/kg to about 15, 20, 50, 100, 150 or 200 mg/kg wherein "mg" refers to the level of the component and "kg" refers to kilograms of body weight of the mammal. In an embodiment, the dosage to the mammal, on a daily basis, may be from about 1 mg/kg to about 15 mg/kg, from about 2 mg/kg to about 10 mg/kg, or from about 2 mg/kg to about 5 mg/kg. In certain embodiments, this may translate to compositions comprising less than about 5%, or less than about 2%, or from about 0.0001% to about 0.5% of the component, all by weight of the composition. The level of component may be determined by one of ordinary skill in the art based on a variety of factors, for example, the form of the composition (e.g., whether a dry composition, semi-moist composition, wet composition, or supplement, or any other form or mixture thereof). The ordinarily skilled artisan will be able to utilize the preferred dosage and determine the optimal level of component within a given composition.

Similarly, wherein an extract or meal of plant matter is utilized in the compositions herein, optimal levels of extract or meal may be dependent upon level of efficacious component within such extract or meal. Optimal extracts and/or meals have been found herein which comprise from about 0.5% to about 99% of the glucose anti-metabolite component, alternatively from about 0.5% to about 75% of the glucose anti-metabolite component, alternatively from about 0.5% to about 50% of the glucose anti-metabolite component, alternatively, from about 0.5% to about 25% of the glucose anti-metabolite component, all by weight of the extract or meal. Optimal extracts and/or meals have been found herein in which the glucose anti-metabolite component may be from about 0.5, 1, 2, 5, or 10% to about 15, 25, 50 or 75% by weight of the extract and/or meal.

The present invention is directed to a composition that is intended for ingestion by a mammal. Compositions include foods intended to supply necessary dietary requirements, as well as treats (e.g., biscuits) or other food supplements. Optionally, the composition herein may be a dry composition (for example, kibble), semi-moist composition, wet composition, or any mixture thereof. Alternatively or additionally, the composition is a supplement, such as a gravy, drinking water, yogurt, powder, suspension, chew, treat (e.g., biscuits) or any other delivery form.

Moreover, in one embodiment the composition is nutritionally balanced. As used herein, the term "nutritionally balanced," with reference to the composition, means that the composition has known required nutrients to sustain life in proper amounts and proportion based on recommendations of recognized authorities in the field of nutrition.

The compositions used herein may optionally comprise one or more further components. Other components are beneficial for inclusion in the compositions used herein, but are optional for purposes of the invention. In one embodiment, the compositions may comprise, on a dry matter basis, from about 10% to about 90% crude protein, alternatively from about 20% to about 50% crude protein, alternatively from about 20% to about 40% crude protein, by weight of the composition, or alternatively from about 20% to about 35% crude protein, by weight of the composition. The crude protein material may comprise vegetable-based proteins such as soybean, cereals (corn, wheat, etc), cottonseed, and peanut, or animal-based proteins such as casein, albumin, and meat protein. Non-limiting examples of meat protein useful herein include a protein source selected from the group consisting of beef, pork, lamb, poultry, fish, and mixtures thereof.

Furthermore, the compositions may comprise, on a dry matter basis, from about 5% to about 40% fat, alternatively from about 10% to about 35% fat, by weight of the composition.

The compositions of the present invention may further comprise a source of carbohydrate. Grains or cereals such as rice, corn, milo, sorghum, barley, wheat, and the like are illustrative sources.

The compositions may also contain other materials such as, but not limited to, dried whey and other dairy by-products, beet pulp, cellulose, fiber, fish oil, flax, vitamins, minerals, flavors, antioxidants, and taurine.

The following non-limiting illustrations exemplify the various glucose anti-metabolites of the present invention:

Decreased Utilization of Glucose as Energy Source by 2-Deoxy-D-Glucose:

To mimic the effects of caloric restriction, glucose anti-metabolites are provided over an extended time period. Previous studies show that 2-deoxy-D-glucose should not be administered in high doses, since significant untoward side effects and toxicity have been observed. However, studies in rodents (Lane et al., J. Anti-Aging Med. 1 (4): 327-337 (1998)) have shown that long-term disruption of glucose metabolism using a lower dose of 2-deoxy-D-glucose can mimic some of the major metabolic hallmarks of caloric restriction and enhanced longevity, including reduced body temperature, weight loss, and lower fasting insulin levels.

In light of the above potential physiologic benefits of caloric restriction weighed against the negative aspects of metabolic inhibition by 2-deoxy-D-glucose, alternatives which act as anti-metabolites of glucose without the potentially harmful side effects are preferred for purposes of practicing the invention.

Decrease of Availability of Glucose to Cells by 5-Thio-D-Glucose:

5-Thioglucose, an analog of glucose, has (in vivo) more pronounced effects than 2-deoxy-D-glucose. The compound is believed to act mainly by inhibiting glucose uptake by the cells. The majority of 5-thioglucose (97%) injected into a rat has been found excreted unchanged in urine (Hoffman et al., Biochemistry 7, pp. 4479-4483 (1968)). 5-Thioglucose is remarkably non-toxic; $LD_{50}$ was measured to be 14 g/kg, by injection, in rats (Chen et al., Arch. Biochem. Biophys., 169, pp. 392-396 (1975)).

Since 5-Thioglucose seems to be excreted unchanged in urine, this compound presents certain advantages for chronic administration over 2-deoxy-D-glucose. Since 5-thioglucose inhibits glucose uptake, appropriate dosing can result in benefits associated with caloric restriction, including enhanced longevity.

Effects of 3-O-Methylglucose:

This analog of glucose, in contrast with 2-deoxy-D-glucose, is not metabolized (Jay et al., J. Neurochem. 55, pp. 989-1000 (1990)) and, thus, may provide certain advantages for use in chronic administration. In the context of this invention, 3-O-methylglucose can prevent utilization of glucose as an energy source as demonstrated by response to its administration in rats. The responses were about seven times weaker than those to 2-deoxyglucose.

Effects of Anhydrosugars: 1,5-Anhydro-D-Glucitol (Polygalitrol):

This compound is a non-reducing analog of glucose and is enzymatically converted to 1,5-anhydro-D-glucitol-6-phosphate, albeit the conversion is less efficient than that of 2-deoxy-glucose (Sols et al., J. Biol. Chem., 210, pp. 581-595 (1954). 1,5-anhydro-D-glucitol-6-phosphate is an allosteric (non-competitive) inhibitor of hexokinase, which catalyzes the first regulatory step of glycolysis (Crane et al., J. Biol. Chem., 210, pp. 597-696 (1954)). Furthermore, 1,5-anhydro-D-glucitol-6-phosphate is a non-reducing analog and cannot be a substrate for the next step of glycolysis catalyzed by glucose-6-phosphate isomerase. Consequently, this analog could accumulate in cells and act as a very effective metabolic block to glucose utilization. Another advantage relating to its non-reducing character is that this compound cannot be incorporated into glycolipids, glycoproteins, and glycogen. Thus, its effects are specific to glycolysis and would not be expected to affect other metabolic processes or exert toxicity of some glucose anti-metabolites previously discussed.

Interestingly, this compound (or its phosphate) has been found in the human body. It was found to be present in cerebrospinal fluid of patients who had occasional high blood glucose (from diabetes and diseases of the kidney) in large enough concentrations to be detected in tests performed in normal clinical settings.

Use of 2,5-Anhydro-D-Mannitol and 2,5-Anhydro-D-Glucitol:

These compounds are non-reducing analogs of fructose. Fructose is an important component of food and fructose phosphates and diphosphate are intermediate products of glycolysis. Nevertheless, inhibition of metabolic events involving fructose and its phosphates by anhydrosugar analogs is difficult. Alpha and beta anomers of fructose, which spontaneously inter-convert, correspond to different anhydrosugars, to 2,5-anhydro-D-glucitol and 2,5-anhydro-D-mannitol, respectively. Thus, only a few of the enzymatic conversions can be inhibited by a single compound. The 2,5-Anhydro-D-mannitol has been investigated in some detail. That compound is taken up by cells and converted into 2,5-anhydro-D-mannitol-1-phosphate. That phosphate is an analog of fructose-1-phosphate, but cannot be cleaved by the aldolase and, thus, the utilization of both glucose and fructose by cells is blocked. The 2,5-Anhydro-D-mannitol had been found to interfere in glucose formation and utilization in isolated rat hepatocytes (Riquelme et al., Proc. Natl. Acad. Sci. USA, 80, pp. 431-435 (1983)).

Decrease of Glucose Utilization as Energy Source by Ketoses:

Mannoheptulose is present in reasonable amounts in some foods (e.g., avocados may contain up to 5% of mannoheptulose, by wet weight) and can be classified as a "generally recognized as safe" substance for human consumption. In studies of metabolism, doses of 10 grams of mannoheptulose were safely administered to humans orally. About 5% of the mannoheptulose ingested was reported to appear in urine after oral administration. The fate of injected mannoheptulose has previously been investigated in rats: 66% was excreted unchanged, 29% was metabolized and, a day after the injection, 5% remained in the body (Simon et al., Arch. Biochem. Biophys, 69, pp. 592-601 (1957)).

The availability of glucose to cells can also be decreased using other dietary supplements than those specifically identified herein which have similar effect on metabolism of glucose that can result in an inhibition of glucose processing.

The methods of the invention may be practiced by administering a component described herein orally or parenterally, though oral administration would be preferred. When lowering of tissue metabolism is desired, as an adjunct to treatment of trauma, the component may be administered intravenously.

In addition to the effects of glucose anti-metabolites on insulin and related metabolism in dogs, mice fed a composition containing, for example, mannoheptulose, also exhibit reduced plasma insulin levels and slightly reduced body weight. Both of these endpoints are closely related to altered glucose and/or carbohydrate metabolism, similar to that elicited by dietary caloric restriction. Even more important from a fundamental metabolic standpoint, fruit flies and/or nematodes fed mannoheptulose exhibit lifespan extension of nearly 50%, an effect comparable to that exerted by caloric restriction in a number of animal species.

EXAMPLES

The following examples are provided to illustrate the invention and are not intended to limit the scope thereof in any manner.

Example 1

Preparation of Mannoheptulose-Containing Avocado Meal

Fresh avocados (Lula variety) were obtained from Fresh King Incorporated (Homestead, Fla.). The avocados were manually split open and the pits were removed and discarded. The remaining skin and pulp were ground through a Hobart Commercial Food Preparation machine (Serial No. 11-10410235) using a 12¼ sieve. The ground avocado was then transferred to an Edwards Freeze Drier (Super Modulyo Model, Crawely, Sussex, England). The freeze drier was set at −20° C. for the first 24 hours, −5° C. for the following 24 hours and 5° C. for the final 72 hours. Upon removal from the freeze drier, the meal was ground to a powder using a Straub Grinding Mill (model 4E, Philadelphia, Pa.). The avocado meal was analyzed and found to contain about 10.35% mannoheptulose, by weight of the meal. It should be noted that the amount of mannoheptulose found in avocados varies with the particular strain and state of ripeness, some avocados having little or no mannoheptulose.

Example 2

Administration of Mannoheptulose-Containing Avocado Meal to Beagle Dogs

The use of mannoheptulose for purposes of maintaining and or attenuating a decline in the health, functional activity, and/or biomarkers of longevity as a result of mimicking caloric restriction was tested in beagle dogs through measurement of insulin reduction. As has been discussed, and is now widely accepted in the art, insulin reduction is a hallmark of caloric restriction and therefore a suitable indicator and/or biomarker.

A total of 12 beagles were utilized for the study and were fed a standard commercial composition (Eukanuba Senior Maintenance Formula) through the study period. Fasting blood samples were drawn 7, 6, 4, and 2 days prior to administration of mannoheptulose. The mannoheptulose was delivered to the dogs in the form of a freeze-dried avocado meal containing from about 10% to about 12% mannoheptulose, by weight of the meal. This preparation was adjusted to provide mannoheptulose doses of 2, 20, and 200 mg/kg body weight (MH-2, MH-20, MH-200, respectively). Fasting blood samples were collected 1, 3, 5, and 7 days after initiation of the administration of mannoheptulose.

Insulin levels were lowered by up to 35% in dogs which had received the avocado meal when compared to those dogs on similar compositions which had not received avocado meal with their compositions. Those changes were similar to the decreases found in animals on caloric restricted diets. In contrast, plasma glucose concentrations of dogs fed the same standard composition which did not contain the avocado meal did not show such effects.

Without intending to be limited by theory, the mechanism by which insulin is reduced relates to the fact that glucose must be metabolized by the pancreas to stimulate insulin secretion (German et al., Proc. Nat. Acad. Sci., 90, 1781-1785 (1993)). Mannoheptulose is thought to inhibit hexokinase, the initial enzyme involved in glucose metabolism. Therefore, reduced insulin levels indicate that mannoheptulose has indeed inhibited glucose metabolism, thereby mimicking caloric restriction. This effect on hexokinase by mannoheptulose would indicate use of mannoheptulose directed at inhibition of tumor growth as an alternative to administration of 2-deoxy-D-glucose. See Board et al., Cancer Res., 55(15): 3278-3285 (1995). Mannoheptulose would present a safe alternative to 2-deoxy-D-glucose, since it would avoid some untoward effects seen when 2-deoxy-D-glucose is administered on a long-term basis.

Example 3

Avocado Extract Containing Enhanced Levels of Mannoheptulose is Prepared in Accordance with the Following Optional Process, and Utilized in Compositions of the Present Invention Whole avocado fruit (about 900 kilograms) is provided. The fruit is split and the pits are removed, either partially or wholly, providing about 225 kilograms of pitted avocado halves. The raw avocado is charged to a disintegrator, whereupon some agitation, water (about 3000 kilograms) and CELLUBRIX (commercially available from Novozymes A/S) (about 1 liter) is further charged. The mixture is further agitated and concurrently heated to about 66° C. Upon completion of the charge, further CELLUBRIX (about 1 liter) is added, and the entire mixture is held under agitation for about 12 hours at a controlled pH of about 5.5. The temperature is then further increased to about 80° C. and then held for at least about 2 hours. The resulting digested plant mixture is then filtered at 80° C. to provide the carbohydrate extract as the filtrate. The carbohydrate extract is then evaporated in a simplified recirculation system at 80° C., under vacuum, to provide the carbohydrate extract having from about 10% to about 20% solids and a pH of about 5.5. The extract is then further concentrated using a refractance window dryer to provide about 100 kilograms of the extract as a crystalline or powder (a yield of about 11% carbohydrate extract, based on the starting mass of the whole avocado fruit, which is analyzed as a yield from about 0.25% to about 4.5% mannoheptulose, based on the starting mass of the whole avocado fruit). It should be noted the amount of mannoheptulose found in avocados varies with the particular strain and state of ripeness of the fruit. The extract may be used in the compositions of the present invention.

Example 4

Table 1 illustrates two kibble compositions having the following components at the approximate indicated amounts are prepared using methods which are standard in the art, including extrusion, and are fed to dogs and/or cats as a daily feed:

TABLE 1

| Component | Example 4A (Component Amount indicated as Wt %) | Example 4B (Component Amount indicated as Wt %) |
|---|---|---|
| Extract of Avocado* | 0.02 | 0.01 |
| Chicken, Chicken By-product Meal, Fish Meal, and Egg | 44 | 47 |
| Chicken Fat | 8 | 6 |
| Beet Pulp | 2 | 3 |
| Salts | 2.5 | 2 |
| Vitamins and Minerals** | 1 | 1 |
| Minors*** | 3.5 | 4 |
| Grains (corn, sorghum, barley, rice, wheat) | Remainder | Remainder |

*Avocado may be substituted with other plant matter having enhanced mannoheptulose content. The incorporation of a mannoheptulose source likely replaces a similar amount of a grain source in the composition.
**Vitamins and Minerals may include: Vitamin E, beta-carotene, Vitamin A, Ascorbic Acid, Calcium Pantothenate, Biotin, Vitamin $B_{12}$, Vitamin $B_1$, Niacin, Vitamin $B_2$, Vitamin $B_6$, Vitamin $D_3$, Vitamin $D_2$, Folic Acid, Choline Chloride, Inositol, Calcium Carbonate, Dicalcium Phosphate, Potassium Chloride, Sodium Chloride, Zinc Oxide, Manganese Sulfate, Copper Sulfate, Manganous Oxide, Ferrous Sulfate, Potassium Iodide, Cobalt Carbonate.
***Minors may include: Fish oil, flax seed, flax meal, cellulose, flavors, antioxidants, taurine, yeast, carnitine, chondroitin sulfate, glucosamine, lutein, rosemary extract.

Example 5

Table 2 Illustrates a Beef-Flavor Gravy Composition is Prepared by Combining the Following Components in a Conventional Manner

TABLE 2

| Component | Wt % |
|---|---|
| Mannoheptulose* | 0.14 |
| Chicken Fat | 3.0 |
| Spray-Dried Beef Particles and Broth | 3.0 |
| Xanthan Gum | 0.5 |
| Flax Seed | 0.2 |
| Vegetables | 0.2 |
| Vitamins** | 0.06 |
| Minerals** | 0.04 |
| Phosphoric Acid | 0.95 |
| Beef Flavor | 0.1 |
| Water | Remainder |

*Mannoheptulose may be substituted with another component as described herein. The incorporation of a mannoheptulose source likely replaces a similar amount of water in the composition.
**Vitamins and Minerals may include: Vitamin E, beta-carotene, Vitamin A, Ascorbic Acid, Calcium Pantothenate, Biotin, Vitamin $B_{12}$, Vitamin $B_1$, Niacin, Vitamin $B_2$, Vitamin $B_6$, Vitamin $D_3$, Vitamin $D_2$, Folic Acid, Choline Chloride, Inositol, Calcium Carbonate, Dicalcium Phosphate, Potassium Chloride, Sodium Chloride, Zinc Oxide, Manganese Sulfate, Copper Sulfate, Manganous Oxide, Ferrous Sulfate, Potassium Iodide, Cobalt Carbonate.

One fluid ounce of the gravy composition is mixed with one-half cup of a standard composition daily prior to feeding to a mammal. Amounts of the gravy composition are determined as desired by the guardian of the mammal.

Example 6

Once Daily Administration of Mannoheptulose in a Nutritionally-Balanced Composition Fed to Adult Labrador Retriever Dogs The pharmacokinetics of mannoheptulose can be determined in six adult, male Labrador Retriever dogs fed a nutritionally-balanced composition providing mannoheptulose at levels of 0, 1 or 2 mg/kg of body weight of the dog. Mannoheptulose is provided as an enriched source of avocado extract in the 1 and 2 mg/kg diets. The mean age of the dogs is 4.2 years and the age ranges from 3.3 to 6.1 years. The average body weight of all dogs is 33 kg and the body weight ranges from 28 to 36 kg. Dogs are adapted for 14 days to a nutritionally-balanced control composition (Eukanuba Senior Maintenance Formula) containing no mannoheptulose, avocado extract or avocado meal (0 mg/kg mannoheptulose). The two compositions containing mannoheptulose are the nutritionally-balanced control composition formulated with avocado extract to provide a mannoheptulose dose of 1 or 2 mg/kg of body weight when fed to a dog. The amount of composition offered to the dogs is based on feeding guidelines for the control composition and the target weight range and body condition of the dogs. After 14 days, dogs are fed one of the three compositions for 9 days. On day 9, the dogs are fed their daily allotment of composition as a single meal at 0730. Dog 1 and dog 2 are fed the control composition containing 0 mg/kg mannoheptulose, dog 3 and dog 4 are fed the composition containing 1 mg/kg mannoheptulose, and dog 5 and dog 6 are fed the composition containing 2 mg/kg mannoheptulose. Pharmacokinetics of mannoheptulose following once daily administration of mannoheptulose in a nutritionally-balanced composition is determined by collecting serial blood samples (3 mL) from each dog on day 9 using a Vacutainer blood collection system and jugular venipuncture. Blood samples are collected at −30, 0, 30, 60, 90, 120, 240, 360, 480, 600, 720 and 1,440 minutes relative to each dog receiving their entire daily allotment of composition as a single meal. Plasma mannoheptulose concentrations are measured using high-performance liquid chromatography tandem mass spectrometry as described herein below.

A one-compartment model is used to calculate mannoheptulose pharmacokinetics based on plasma mannoheptulose levels following once daily oral administration of mannoheptulose in a nutritionally-balanced composition ($P_{V(t)}$). The model is: $P_{V(t)} = \text{dose}/(a \cdot BW)e^{-kt}$ where: a=mannoheptulose pool size (dose/(enrichment at $t_0$)), BW=body weight, k=rate constant of elimination (ln $E_t$−ln $E_0$)/−t, and t=time. Area under each plasma mannoheptulose curve is determined using a one-way, repeated measures analysis of variance (GraphPad Prism version 4.00 for Windows).

FIG. 1 is a graphical presentation of the serial concentrations of plasma mannoheptulose in adult Labrador Retrievers fed a single meal of a nutritionally-balanced composition containing mannoheptulose at a dose of 0 mg/kg (dogs 1 and 2), 1 mg/kg (dogs 3 and 4) or 2 mg/kg (dogs 5 and 6). Plasma mannoheptulose reaches peak concentrations in adult dogs between 6 and 8 hours after the consumption of a single meal of a composition containing mannoheptulose. Plasma mannoheptulose concentrations return to non-detectable levels by 24-hours after consumption of the single daily meal. Plasma mannoheptulose follows first order kinetics with the once daily oral administration of 1 or 2 mg/kg of mannoheptulose in a nutritionally-balanced composition. Mathematical modeling shows mannoheptulose has a half-life of 6.25 hours and a turnover time of 9.0 hours following once daily oral administration of mannoheptulose (2 mg/kg) in a nutritionally-balanced composition. Plasma mannoheptulose levels respond to dietary mannoheptulose levels in a dose-dependent manner. Feeding a composition containing 2 mg/kg mannoheptulose results in higher plasma mannoheptulose concentrations compared with feeding compositions containing 0 and 1 mg/kg mannoheptulose. Mannoheptulose is not detected in the plasma of dogs consuming a composition containing 0 mg/kg mannoheptulose. Area under the curve is significantly different for all three compositions and is dependent on the oral dose of mannoheptulose administered to the dog. There is no measurable area under the plasma mannoheptulose curve for dogs consuming a composition devoid of mannoheptulose compared with greater areas under the curve with compositions that provide 1 or 2 mg/kg of mannoheptulose per body weight of the dog.

Example 7

Twice Daily Administration of Mannoheptulose in a Nutritionally-Balanced Composition Fed to Older Labrador Retriever Dogs The pharmacokinetics of mannoheptulose can be determined in ten adult, female Labrador Retriever dogs fed a nutritionally-balanced composition providing mannoheptulose at levels of 0 or 2 mg/kg of body weight of the dog. Mannoheptulose is provided as avocado extract in the 2 mg/kg diet. The mean age of the dogs is 7.1 years and the age ranges from 5.3 to 8.4 years. Dogs are age-matched across the two composition groups. The average body weight of all dogs is 29 kg and ranges from 25 to 35 kg. The 0 mg/kg composition is fed as a nutritionally-balanced control composition (Eukanuba Senior Maintenance Formula) and it contains no mannoheptulose, avocado extract or avocado meal. The 2 mg/kg composition is the nutritionally-balanced control composition formulated to contain avocado extract to provide mannoheptulose at a dose of 2 mg/kg of body weight of the dog. The amount of composition offered to the dogs is based on feeding guidelines for the control composition and the target weight range and body condition of the dogs. Dogs are fed one-half their daily allotment of composition at 0730 and the remaining half at 1330. Dogs 1, 2, 3, 4 and 5 are fed the composition containing 2 mg/kg mannoheptulose and dogs 6, 7, 8, 9 and 10 are fed the composition containing 0 mg/kg mannoheptulose. Pharmacokinetics of mannoheptulose following twice daily administration of mannoheptulose in a nutritionally-balanced composition is determined by collecting serial blood samples (3 mL) from each dog using a Vacutainer blood collection system and jugular venipuncture. Blood samples are collected at 0, 120, 240, 360, 480, 600, 720 and 1,440 minutes relative to each dog receiving their entire daily allotment of composition in two separate but equal meals. Plasma mannoheptulose concentrations are measured using high-performance liquid chromatography tandem mass spectrometry as described herein below.

A one-compartment model is used to calculate mannoheptulose pharmacokinetics based on plasma mannoheptulose levels following twice daily oral administration of mannoheptulose in a nutritionally-balanced composition ($P_{V(t)}$). The model is: $P_{V(t)} = \text{dose}/(a \cdot BW)e^{-kt}$ where: a=mannoheptulose pool size (dose/(enrichment at $t_0$)), BW=body weight, k=rate constant of elimination (ln $E_t$−ln $E_0$)/−t, and t=time.

Figure 2:
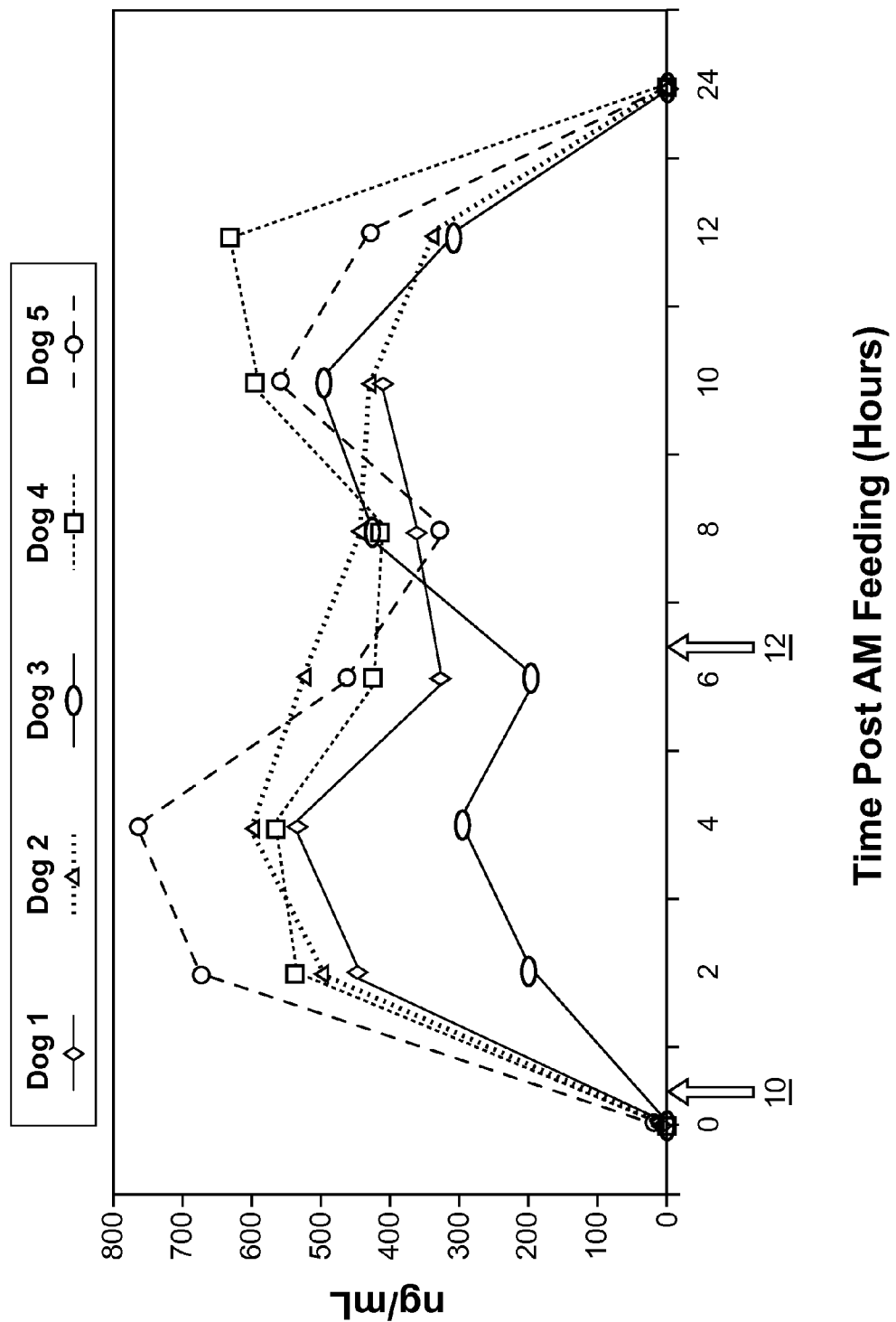
FIG. 2 is a graphical presentation of serial concentrations of plasma mannoheptulose in adult Labrador Retrievers fed two equal meals of a nutritionally balanced composition containing mannoheptulose at a dose of 2 mg/kg of the body weight of the dog.

FIG. 2 is a graphical presentation of the serial concentrations of plasma mannoheptulose in adult Labrador Retrievers fed two equal meals of a nutritionally-balanced composition containing mannoheptulose at a dose of 2 mg/kg of body weight (dogs 1, 2, 3, 4 and 5). No detectable mannoheptulose is present in the plasma of dogs fed the nutritionally-balanced composition devoid of mannoheptulose (0 mg/kg). Plasma mannoheptulose levels rise from undetectable levels at time of initial feeding 10 to peak levels in 4 hours in dogs fed a nutritionally-balanced composition containing avocado extract to provide mannoheptulose at a dose of 2 mg/kg of body weight. A second peak in plasma mannoheptulose concentrations occurs 4 hours after feeding an afternoon meal 12 of the same composition containing mannoheptulose at a dose of 2 mg/kg of body weight. Plasma mannoheptulose concentrations return to undetectable levels by the following morning. Similar to once daily oral administration, plasma mannoheptulose follows first order kinetics with twice daily oral administration of mannoheptulose in a nutritionally-balanced composition that provides mannoheptulose at a level of 2 mg/kg of body weight. Mathematical modeling shows twice daily oral administration of mannoheptulose in a nutritionally-balanced composition results in a mannoheptulose half-life of 5.42 hours and a turnover time of 7.8 hours after the morning meal and a half-life of 5.63 hours and a turnover time of 3.90 hours after the afternoon meal.

Example 8

Long-Term Administration of Mannoheptulose in a Nutritionally-Balanced Composition Fed to a Cohort of Older Adult Labrador Retriever Dogs A total of 39 older Labrador Retrievers are fed a nutritionally-balanced composition providing mannoheptulose at levels of 0 or 2 mg/kg of body weight of the dog. Average age of the dogs (12 neutered males, 27 spayed females) at the start of a 4-year study is 6.7 years with a range of 5.1 to 8.2 years of age for the youngest and oldest dog within the cohort, respectively. The 0 mg/kg composition is fed as a nutritionally-balanced control composition (Eukanuba Senior Maintenance Formula) and it contains no mannoheptulose, avocado extract or avocado meal. The 2 mg/kg composition is the nutritionally-balanced control composition formulated with avocado extract to provide mannoheptulose at a dose of 2 mg/kg body weight of the dog. The nutritionally-balanced composition containing 0 mg/kg mannoheptulose is referred to as Diet 1 within this Example. The nutritionally-balanced composition containing 2 mg/kg mannoheptulose is referred to as Diet 2 within this Example. The daily food allowance for each older dog is based on the amount of food required to maintain the target body weight and body condition of each dog as described herein below in the Animal Feeding Management Method. Older dogs are fed one-half their daily allotment of food at 0730 and 1430 each day. Consumption of the nutritionally-balanced compositions by older dogs during years 1, 2, 3 and 4 averages 436, 409, 392 and 385 g/day for dogs fed Diet 1 and 428, 389, 392 and 390 g/day for dogs fed Diet 2, respectively. Monthly, quarterly, biannually and/or annual measurements are used to assess the maintenance and/or attenuation in the decline of the quality of life of the mammal.

Table 3 shows the body weight at year 0 and year 4 of older dogs fed Diet 1 and Diet 2.

TABLE 3

| Older dogs | Year | Diet 1 | | | Diet 2 | | |
| --- | --- | --- | --- | --- | --- | --- | --- |
| | | Mean | Min | Max | Mean | Min | Max |
| Body weight, kg | 0 | 28.4 | 19.2 | 35.2 | 28.9 | 20.2 | 41.4 |
| | 4 | 30.7 | 22.4 | 39.4 | 31.5 | 24.3 | 40.0 |

Figure 3:
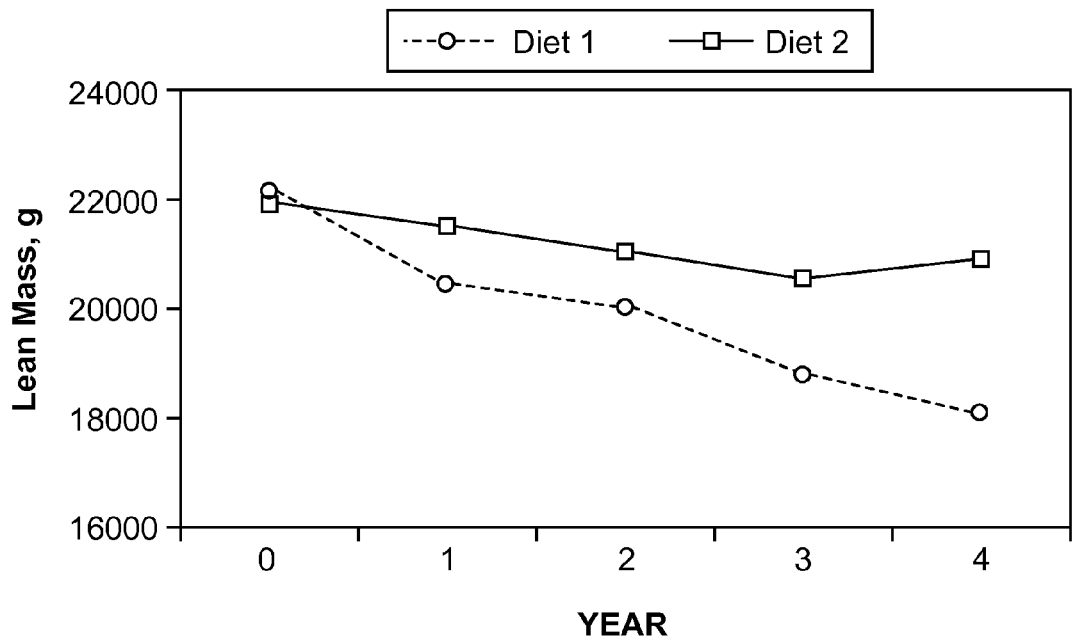
FIG. 3 is a graphical presentation of the average yearly lean body mass of older dogs over a 4 year period of feeding a nutritionally balanced composition containing mannoheptulose at a dose of 0 or 2 mg/kg of the body weight of the dog.

FIG. 3 is a graphical presentation of the average yearly lean body mass of older dogs over 4 years of feeding nutritionally-balanced compositions that provide mannoheptulose at levels of 0 mg/kg (Diet 1) or 2 mg/kg (Diet 2) of body weight of the dog. Lean body mass of individual dogs is measured annually by DEXA as described herein below. As older dogs increase in average age from 6.7 to 10.7 years, the amount of lean body mass does not change appreciably when consuming a nutritionally-balanced composition containing mannoheptulose at a level of 2 mg/kg of body weight. In contrast, older dogs consuming a nutritionally-balanced composition devoid of mannoheptulose steadily lose lean body mass over 4 years. Mannoheptulose provided as avocado extract in a nutritionally-balanced composition maintains and/or attenuates the decline of lean body mass of older dogs as they age.

Figure 4:
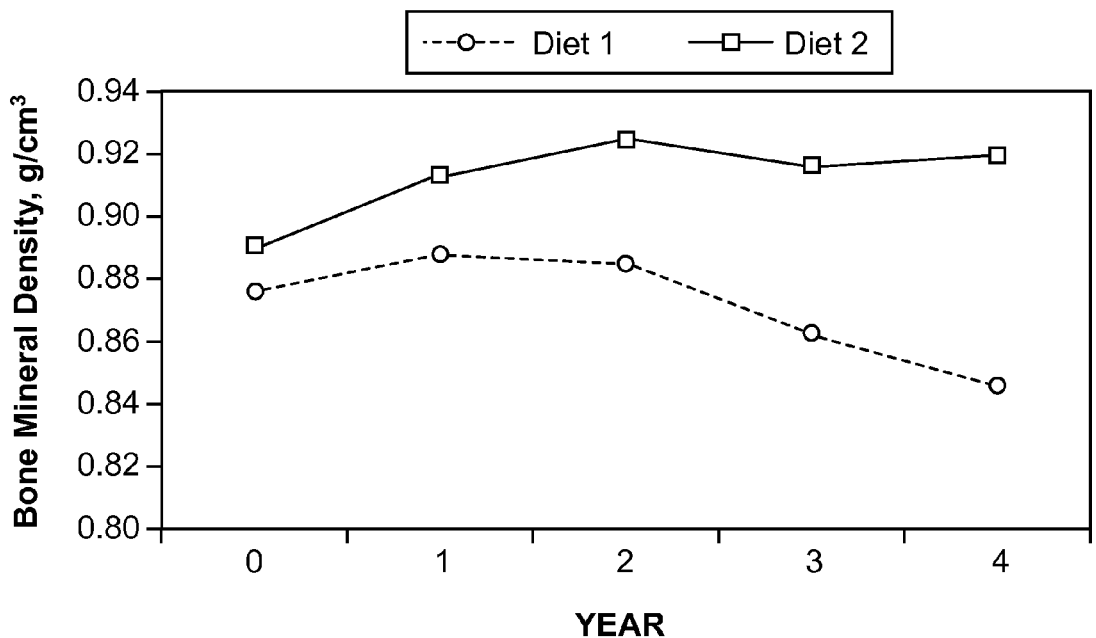
FIG. 4 is a graphical presentation of the average yearly bone mineral density of older dogs over a 4 year period of feeding a nutritionally balanced composition containing mannoheptulose at a dose of 0 or 2 mg/kg of the body weight of the dog.

FIG. 4 is a graphical presentation of the average yearly bone mineral density of older dogs over 4 years of feeding nutritionally-balanced compositions that provide mannoheptulose at levels of 0 mg/kg (Diet 1) or 2 mg/kg (Diet 2) of body weight of the dog. Bone mineral density of individual dogs is measured annually by DEXA as described herein below. As older dogs increase in average age from 6.7 to 10.7 years, maintenance and/or attenuation in the decline of bone mineral density is observed when consuming a nutritionally-balanced composition containing mannoheptulose at a level of 2 mg/kg of body weight. In contrast, a decline in bone mineral density is observed in older dogs consuming a nutritionally-balanced composition devoid of mannoheptulose beginning at year 2 with a steady decline thereafter. Mannoheptulose provided as avocado extract in a nutritionally-balanced composition maintains and/or attenuates a decline in bone mineral density of older dogs as they age.

Figure 5:
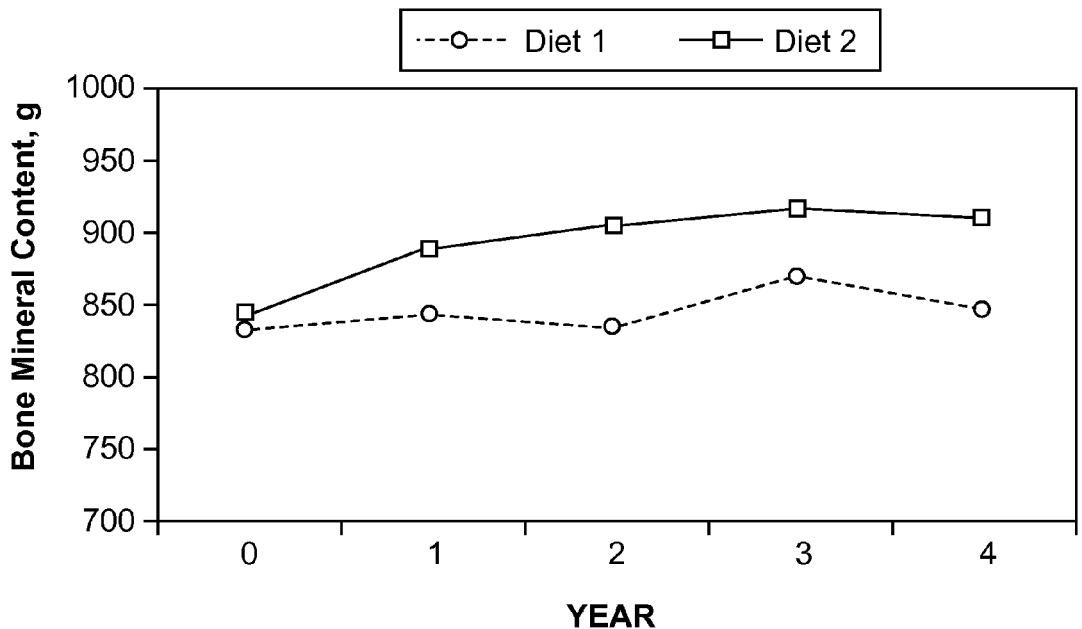
FIG. 5 is a graphical presentation of the average yearly bone mineral content of older dogs over a 4 year period of feeding a nutritionally balanced composition containing mannoheptulose at a dose of or 2 mg/kg of the body weight of the dog.

FIG. 5 is a graphical presentation of the average yearly bone mineral content of older dogs over 4 years of feeding nutritionally-balanced compositions that provide mannoheptulose at levels of 0 mg/kg (Diet 1) or 2 mg/kg (Diet 2) of body weight of the dog. Bone mineral content of individual dogs is measured annually by DEXA as described herein below. As older dogs increase in average age from 6.7 to 10.7 years, enhancement of bone mineral content is observed within the first year and bone mineral content continues to increase thereafter when consuming a nutritionally-balanced composition containing mannoheptulose at a level of 2 mg/kg of body weight. In contrast, older dogs consuming a nutritionally-balanced composition devoid of mannoheptulose show no appreciable change in bone mineral content over 4 years except for a transient increase in year 3 that returns to previous levels by year 4. Mannoheptulose provided as avocado extract in a nutritionally-balanced composition maintains or enhances bone mineral content of older dogs as they age.

Figure 6:
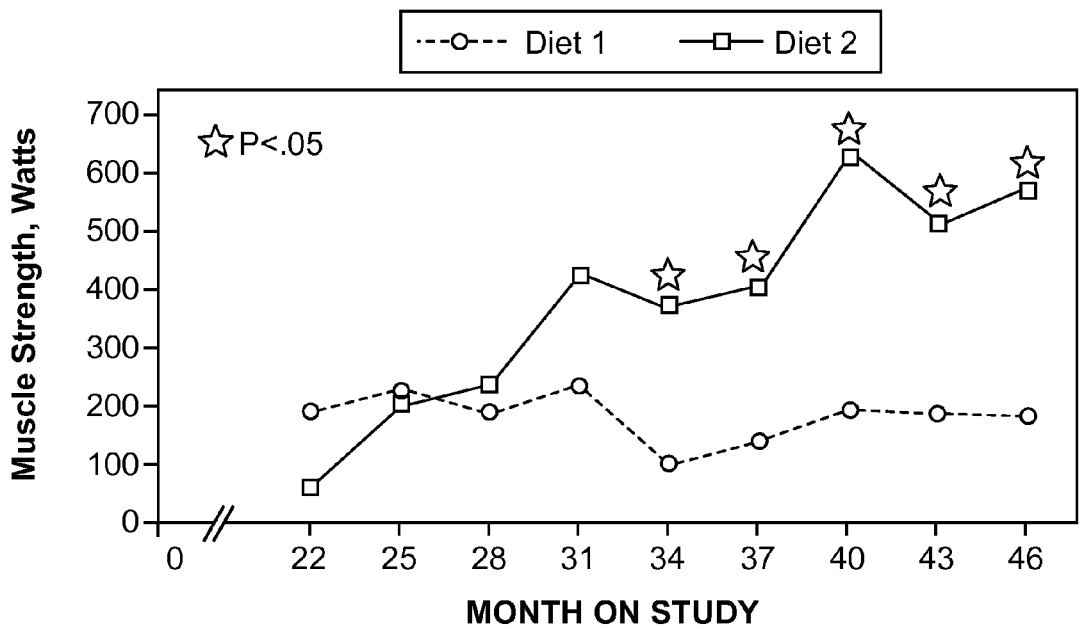
FIG. 6 is a graphical presentation of the average muscle strength, expressed as muscle power, of older dogs during months 19 through 46 of a 4 year period of feeding nutritionally balanced compositions containing mannoheptulose at a dose of 0 or 2 mg/kg of the body weight of the dog. The initial muscle strength is reported at month 22 of the study.

FIG. 6 is a graphical presentation of the average muscle strength expressed as muscle power of older dogs during 4 years of feeding nutritionally-balanced compositions that provide mannoheptulose at levels of 0 mg/kg (Diet 1) or 2 mg/kg (Diet 2) of body weight of the dog. Muscle strength of individual dogs is determined monthly beginning at month 19 as described herein below. Data are pooled quarterly for analysis and reporting beginning with month 22. By month 31, muscle strength is higher in older dogs consuming a nutritionally-balanced composition containing mannoheptulose at a level of 2 mg/kg of body weight. Muscle strength continue to improve with long-term oral administration of mannoheptulose in a nutritionally-balanced composition. In contrast, muscle strength does not increase over time and remains constant for older dogs consuming a nutritionally-balanced composition devoid of mannoheptulose. Mannoheptulose provided as avocado extract in a nutritionally-balanced composition maintains, and/or enhances muscle strength of older dogs as they age.

Figure 7:
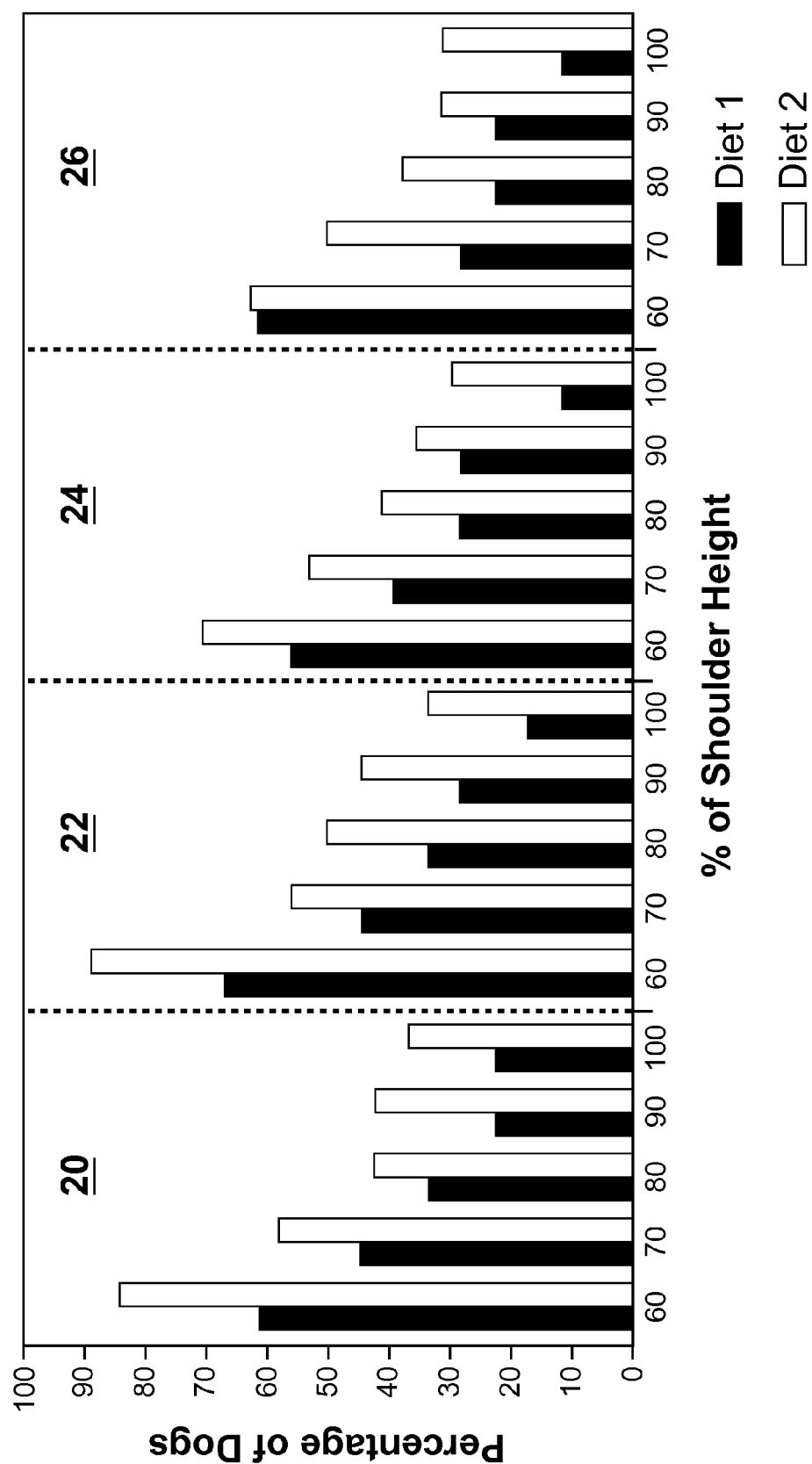
FIG. 7 is a graphical presentation of the percentage of older dogs successfully jumping over various heights relative to their individual shoulder height over one year of a 4 year period of feeding nutritionally balanced compositions containing mannoheptulose at a dose of 0 or 2 mg/kg of body weight of the dog. Jumping ability is assessed during 4 consecutive quarters beginning in month 37.

FIG. 7 is a graphical presentation of the percentage of older dogs successfully jumping over various heights relative to their individual shoulder height during four consecutive quarters of a 4 year period of feeding nutritionally-balanced compositions that provide mannoheptulose at levels of 0 mg/kg (Diet 1) or 2 mg/kg (Diet 2) of body weight of the dog.

Jumping ability of individual dogs is determined quarterly as described herein below. The initial assessment (start of first quarter) is made at month 37 of the study and continues for one year. The four consecutive quarters are represented as reference numbers 20, 22, 24 and 26, respectively in FIG. 7.

Table 4 shows least-squares means for measured shoulder heights of older dogs fed Diet 1 and Diet 2 and the probability value of the pair-wise comparison between the two groups. Shoulder height of the individual dog is used herein below as the standard to assess individual jumping ability. The maximum height successfully jumped by an individual dog is expressed as a percentage of their individual shoulder height. A reported p-value greater than 0.10 indicates no significant difference in shoulder height for older dogs assigned to Diet 1 and Diet 2.

TABLE 4

| Older dogs | Diet 1 | Diet 2 | P-value |
|---|---|---|---|
| Shoulder height, cm | 21.6 | 21.9 | 0.494 |

Table 5 shows the probability value for the pair-wise comparison across all four quarters for the percentage of older dogs fed Diet 1 and Diet 2 that successfully jump a height relative to their individual shoulder height. The assessment of functional capacity is based on the ability of older dogs to successfully jump heights that range from 60 to 100% of their individual shoulder height. A reported p-value less than or equal to 0.10 indicates a statistically significant difference between Diet 1 and Diet 2 across all four test quarters for the percentage of dogs successfully jumping similar heights.

TABLE 5

| | Successful jumping height as a percentage of shoulder height, % | | | | |
|---|---|---|---|---|---|
| | 60 | 70 | 80 | 90 | 100 |
| P-value comparing Diet 1 vs. Diet 2 | .043 | .074 | .097 | .089 | .016 |

A greater percentage of dogs can successfully jump heights that are typically considered non-strenuous for normal, healthy dogs (60 or 70% of their shoulder height). As jumping height increases to 80, 90 or 100% of their shoulder height, a smaller percentage of older dogs can successfully jump these heights demonstrating a more demanding and physically challenging activity and/or test for older dogs. Across all four quarters, a greater percentage of older dogs are able to successfully jump all heights when consuming a nutritionally-balanced composition containing mannoheptulose at a level of 2 mg/kg of body weight as compared with dogs consuming a nutritionally-balanced composition devoid of mannoheptulose. Mannoheptulose provided as avocado extract in a nutritionally-balanced composition maintains and/or attenuates a decline in the jumping ability of older dogs as they age.

Figure 8:
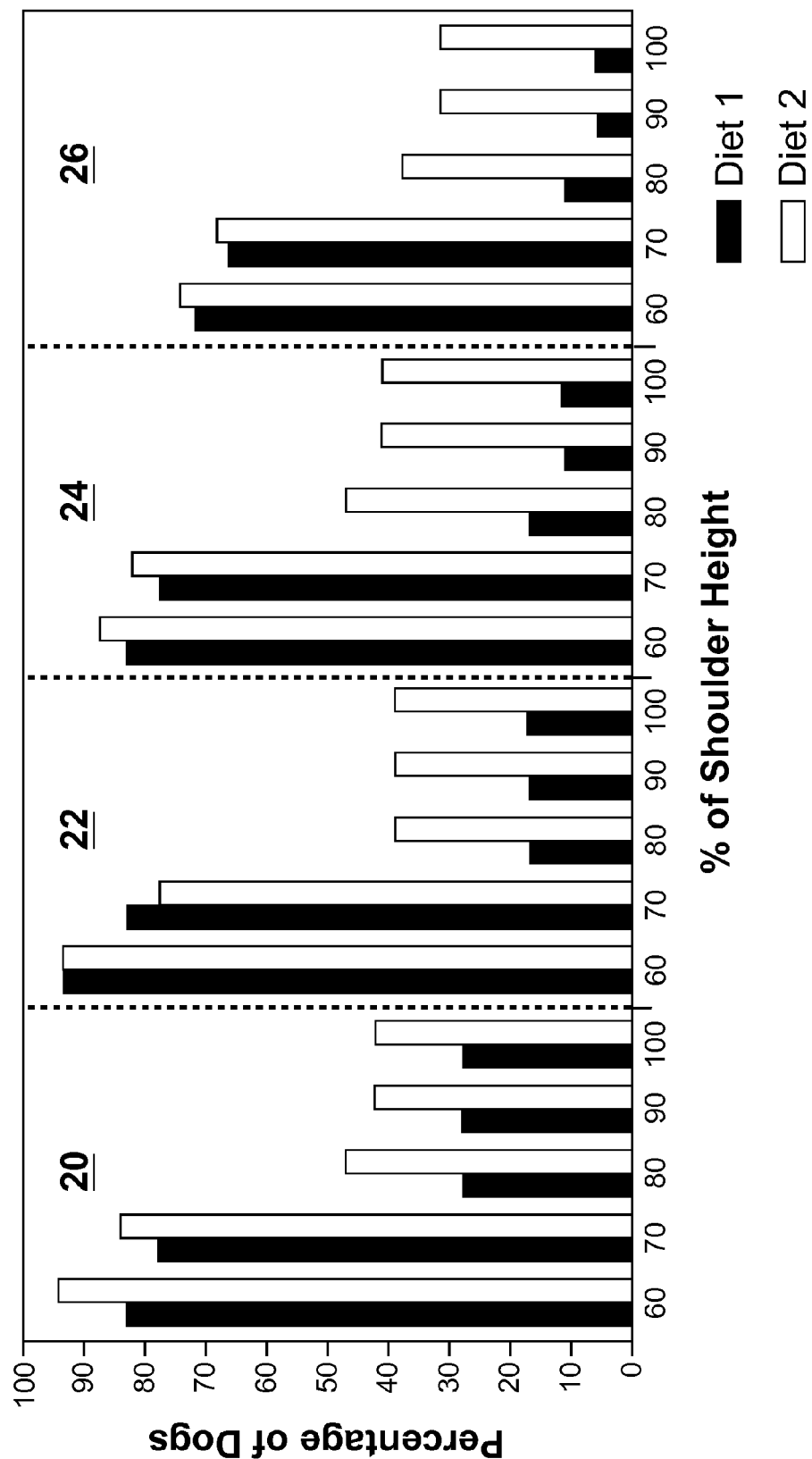
FIG. 8 is a graphical presentation of the percentage of older dogs successfully jumping onto table platforms of various heights relative to their individual shoulder height over one year of a 4 year period of feeding nutritionally balanced compositions containing mannoheptulose at a dose of 0 or 2 mg/kg of body weight of the dog. Jumping ability is assessed during 4 consecutive quarters beginning in month 37.

FIG. 8 is a graphical presentation of the percentage of older dogs successfully jumping onto table platforms of varying heights relative to their individual shoulder height during four consecutive quarters of a 4 year period of feeding nutritionally-balanced compositions that provide mannoheptulose at levels of 0 mg/kg (Diet 1) or 2 mg/kg (Diet 2) of body weight of the dog. Jumping ability of individual dogs is determined quarterly as described herein below. The initial assessment (start of first quarter) is made at month 37 of the study and continues for one year. The four consecutive quarters are represented as reference numbers 20, 22, 24 and 26, respectively, in FIG. 8.

Table 6 shows the probability value for the pair-wise comparison across all four quarters for the percentage of older dogs fed Diet 1 and Diet 2 that successfully jump onto table platforms of increasing height relative to their individual shoulder height. The assessment of functional capacity is based on the ability of dogs to successfully jump onto table platforms of differing heights that range from 60 to 100% of their individual shoulder height. A reported p-value less than or equal to 0.10 indicates a statistically significant difference between Diet 1 and Diet 2 across all four test quarters for the percentage of dogs successfully jumping onto table platforms of similar heights. A reported p-value that is greater than 0.10 indicates a similar jumping ability for both groups across all four quarters.

TABLE 6

| | Platform height as a percentage of shoulder height, % | | | | |
|---|---|---|---|---|---|
| | 60 | 70 | 80 | 90 | 100 |
| P-value comparing Diet 1 vs. Diet 2 | .402 | .074 | .001 | .002 | .002 |

A greater percentage of dogs can successfully jump onto platform heights that are typically considered non-strenuous for normal, healthy dogs (60 or 70% of their shoulder height). As the platform height increases to 80, 90 or 100% of their individual shoulder height, a smaller percentage of older dogs can successfully jump onto taller platforms demonstrating a more demanding and physically challenging activity and/or test for older dogs. Across all four quarters, a greater percentage of older dogs can successfully jump onto platforms that are 70, 80, 90 and 100% of their shoulder height when consuming a nutritionally-balanced composition containing mannoheptulose at a level of 2 mg/kg of body weight. The improved jumping success at the higher platform heights is maintained during all four testing quarters as compared with dogs fed a nutritionally-balanced composition devoid of mannoheptulose as their jumping success declined over time. Mannoheptulose provided as avocado extract in a nutritionally-balanced composition maintains and/or attenuates a decline in the jumping ability of older dogs as they age.

Example 9

Long-Term Administration of Mannoheptulose in a Nutritionally-Balanced Composition to a Cohort of Younger Adult Labrador Retriever Dogs A total of 41 younger Labrador Retrievers are fed a nutritionally-balanced composition providing mannoheptulose at levels of 0 or 2 mg/kg of body weight of the dog. Average age of the dogs (12 neutered males, 29 spayed females) at the start of the 36-month feeding study is 4.0 years with a range of 2.0 to 6.1 years of age for the youngest and oldest dog within the cohort, respectively. The 0 mg/kg composition is fed as a nutritionally-balanced control composition (Eukanuba Senior Maintenance Formula) and it contains no mannoheptulose, avocado extract or avocado meal. The 2 mg/kg composition is the nutritionally-balanced control composition formulated with avocado extract to provide mannoheptulose at a dose of 2 mg/kg body weight of the dog. The nutritionally-balanced composition containing 0 mg/kg mannoheptulose is referred to as Diet 1 within this Example. The nutritionally-balanced composition containing 2 mg/kg mannoheptulose is referred to as Diet 2 within this Example. The daily food allowance for each younger dog is based on the amount of food required to maintain the target body weight and body condition of each dog as described herein below in the Animal Feeding Management Method. Younger dogs are fed one-half their daily allotment of food at 0730 and 1430 each day. Consumption of the nutritionally-balanced compositions by younger dogs during years 1, 2 and 3 averages 419, 354 and 384 g/day for dogs fed Diet 1 and 443, 373 and 402 g/day for dogs fed Diet 2, respectively. Monthly, quarterly, biannually and/or annual measurements are used to assess the maintenance and/or attenuation in the decline of the quality of life of the mammal.

Table 7 shows the body weight at year 0 and year 3 of younger dogs fed Diet 1 and Diet 2.

TABLE 7

| Younger dogs | Year | Diet 1 | | | Diet 2 | | |
| --- | --- | --- | --- | --- | --- | --- | --- |
| | | Mean | Min | Max | Mean | Min | Max |
| Body weight, kg | 0 | 28.7 | 19.9 | 39.7 | 29.0 | 22.8 | 36.6 |
| | 3 | 28.7 | 21.7 | 38.9 | 28.3 | 23.7 | 34.9 |

Figure 9:
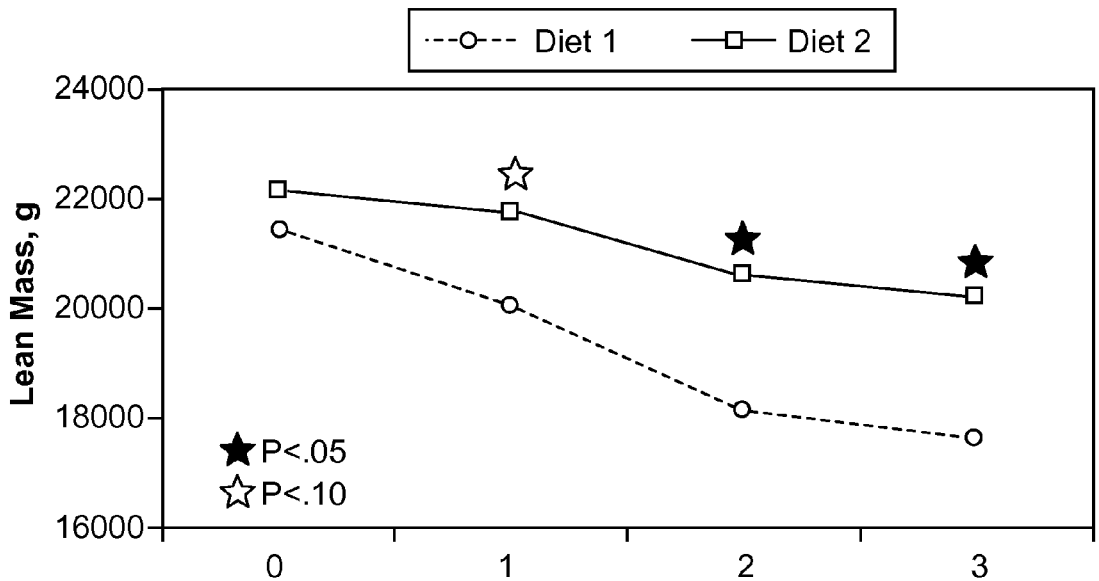
FIG. 9 is a graphical presentation of the average yearly lean body mass of younger dogs over a 3 year period of feeding a nutritionally balanced composition containing mannoheptulose at a dose of 0 or 2 mg/kg of the body weight of the dog.

FIG. 9 is a graphical presentation of the average yearly lean body mass of younger dogs over 3 years of feeding nutritionally-balanced compositions that provide mannoheptulose at levels of 0 mg/kg (Diet 1) or 2 mg/kg (Diet 2) of body weight of the dog. Lean body mass of individual dogs is measured annually by DEXA as described herein below. As younger dogs increase in average age from 4.0 to 7.0 years, the amount of lean body mass does not change appreciably when consuming a nutritionally-balanced composition containing mannoheptulose at a level of 2 mg/kg of body weight. In contrast, younger dogs consuming a nutritionally-balanced composition devoid of mannoheptulose lose more lean body mass over 3 years. Mannoheptulose provided as avocado extract in a nutritionally-balanced compositions maintains and/or attenuates a decline in the lean body mass of younger dogs as they age.

Figure 10:
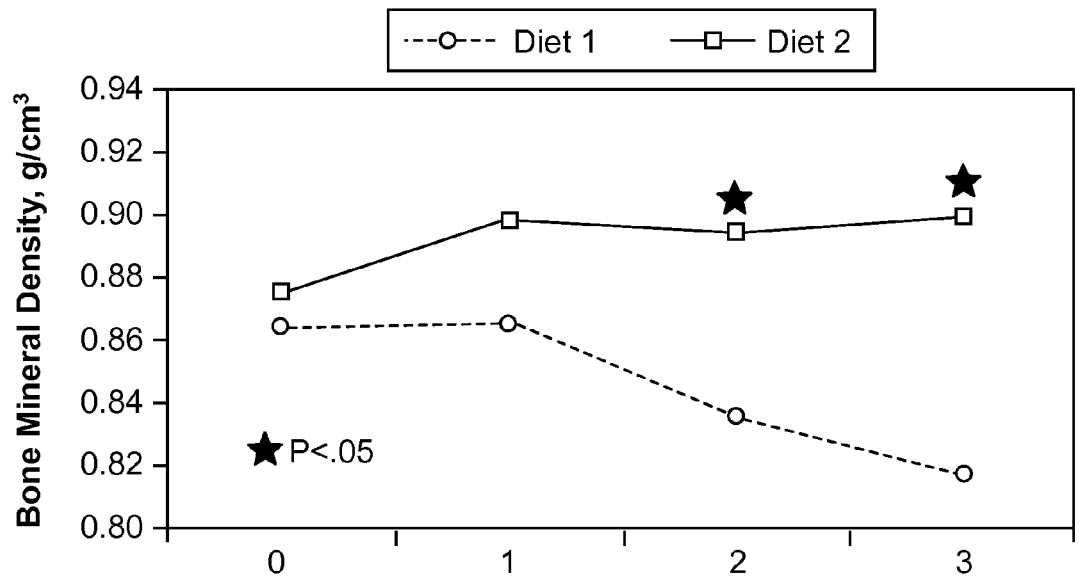
FIG. 10 is a graphical presentation of the average yearly bone mineral density of younger dogs over a 3 year period of feeding a nutritionally balanced composition containing mannoheptulose at a dose of 0 or 2 mg/kg of the body weight of the dog.

FIG. 10 is a graphical presentation of the average yearly bone mineral density of younger dogs over 3 years of feeding nutritionally-balanced compositions that provide mannoheptulose at levels of 0 mg/kg (Diet 1) or 2 mg/kg (Diet 2) of body weight of the dog. Bone mineral density of individual dogs is measured annually by DEXA as described herein below. As younger dogs increase in average age from 4.0 to 7.0 years, maintenance and/or enhancement of bone mineral density is observed when consuming a nutritionally-balanced composition containing mannoheptulose at a level of 2 mg/kg of body weight. In contrast, a decline in bone mineral density is observed in younger dogs consuming a nutritionally-balanced composition devoid of mannoheptulose beginning after year 1 with a steady decline thereafter. Mannoheptulose provided as avocado extract in a nutritionally-balanced composition maintains and/or attenuates a decline in bone mineral density of younger dogs as they age.

Figure 11:
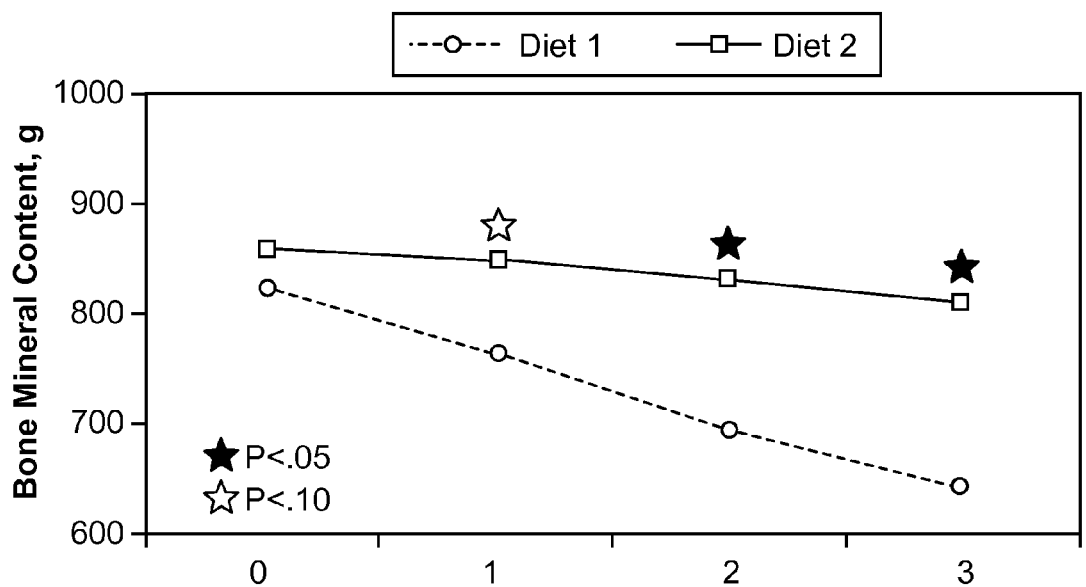
FIG. 11 is a graphical presentation of the average yearly bone mineral content of younger dogs over a 3 year period of feeding a nutritionally balanced composition containing mannoheptulose at a dose of 0 or 2 mg/kg of the body weight of the dog.

FIG. 11 is a graphical presentation of the average yearly bone mineral content of younger dogs over 3 years of feeding nutritionally-balanced compositions that provide mannoheptulose at levels of 0 mg/kg (Diet 1) or 2 mg/kg (Diet 2) of body weight of the dog. Bone mineral content of individual dogs is measured annually by DEXA as described herein below. As younger dogs increase in average age from 4.0 to 7.0 years, bone mineral content declines slightly when consuming a nutritionally-balanced composition containing mannoheptu-lose at a level of 2 mg/kg of body weight. In contrast, younger dogs consuming a nutritionally-balanced composition devoid of mannoheptulose show a decline in bone mineral content over 3 years. Mannoheptulose provided as avocado extract in a nutritionally-balanced composition maintains and/or attenuates a decline in the bone mineral content of younger dogs as they age.

Figure 12:
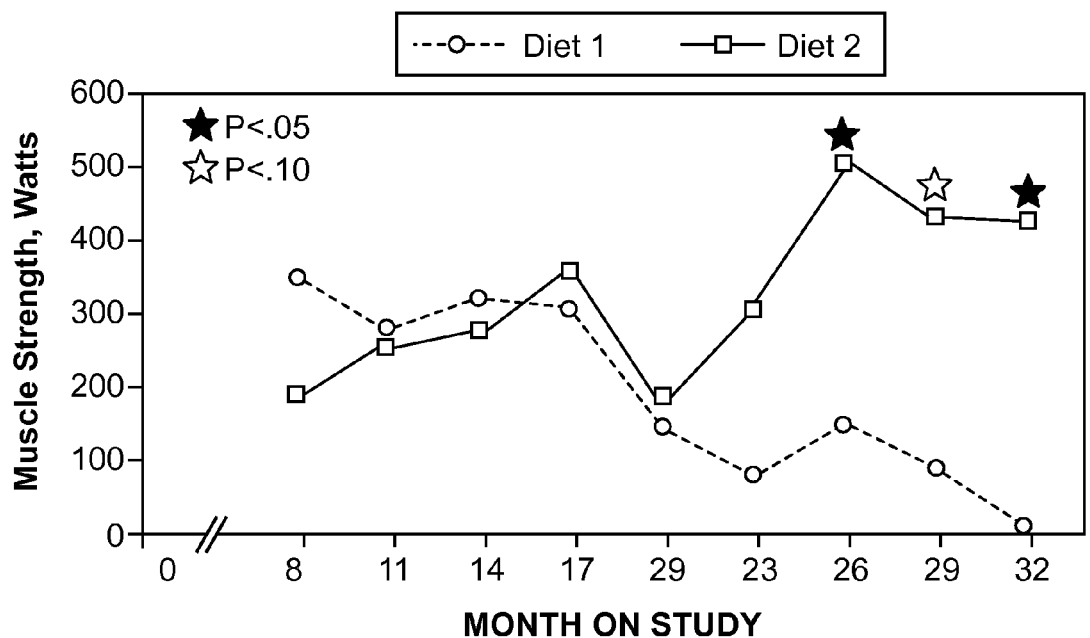
FIG. 12 is a graphical presentation of the average muscle strength, expressed as muscle power, of younger dogs during months 6 through 32 of a 3 year period of feeding nutritionally balanced compositions containing mannoheptulose at a dose of 0 or 2 mg/kg of the body weight of the dog. The initial muscle strength is reported at month 8 of the study.

FIG. 12 is a graphical presentation of the average muscle strength expressed as muscle power of younger dogs during 3 years of feeding nutritionally-balanced compositions that provide mannoheptulose at levels of 0 mg/kg (Diet 1) or 2 mg/kg (Diet 2) of body weight of the dog. Muscle strength of individual dogs is determined monthly beginning from month 6 as described herein below. Data are pooled quarterly for analysis and reporting beginning with month 8. By month 23, muscle strength is higher in younger dogs consuming a nutritionally-balanced composition containing mannoheptulose at a level of 2 mg/kg of body weight. Muscle strength continues to improve with long-term oral administration of mannoheptulose in a nutritionally-balanced composition. In contrast, muscle strength does not increase over time and declines following month 20 for younger dogs consuming a nutritionally-balanced composition devoid of mannoheptulose. Mannoheptulose provided as avocado extract in a nutritionally-balanced composition maintains and/or attenuates a decline in muscle strength of younger dogs as they age.

Figure 13:
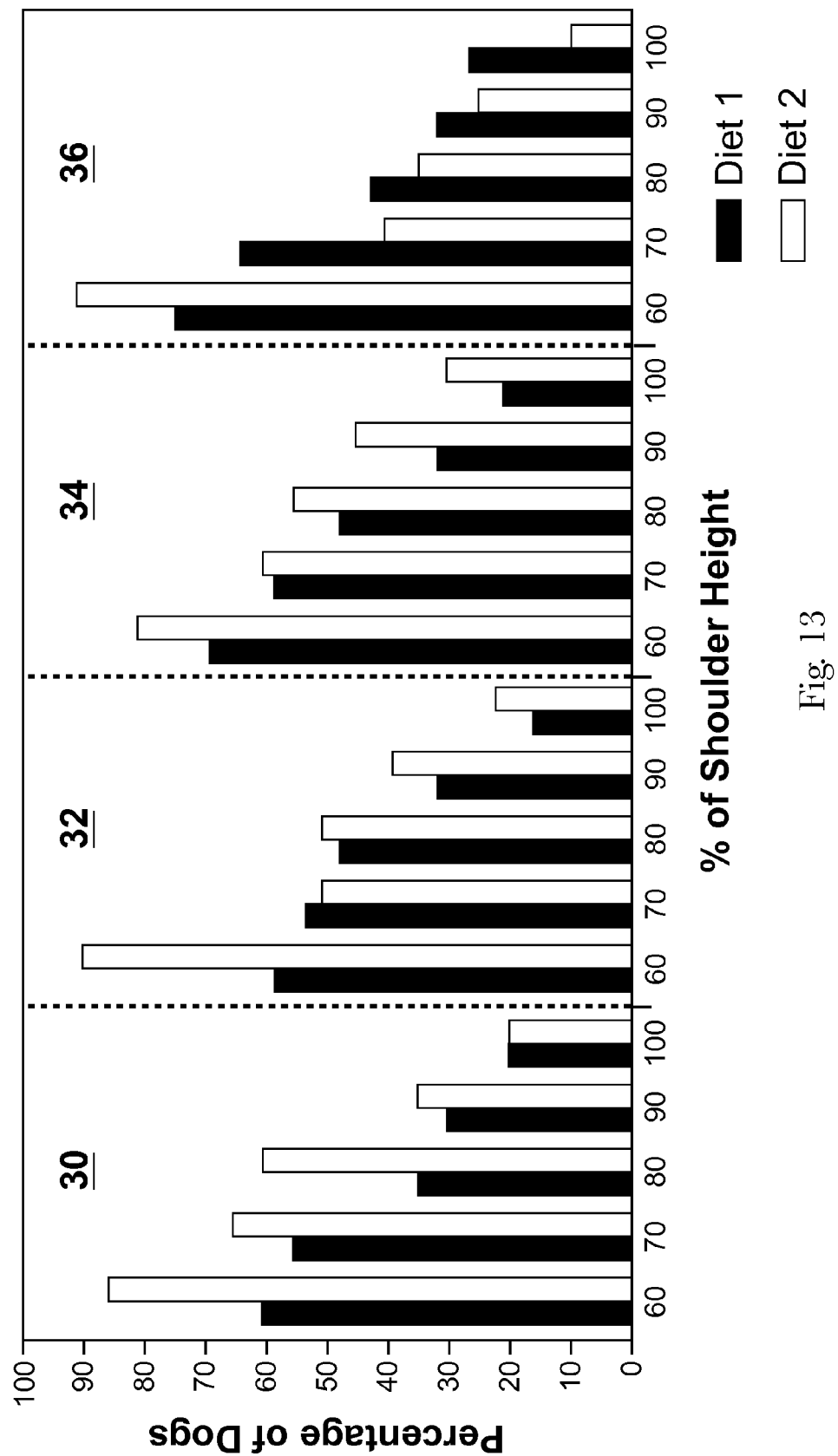
FIG. 13 is a graphical presentation of the percentage of younger dogs successfully jumping over various heights relative to their individual shoulder height over one year of a 3 year period of feeding nutritionally balanced compositions containing mannoheptulose at a dose of 0 or 2 mg/kg of body weight of the dog. Jumping ability is assessed during 4 consecutive quarters beginning in month 8.

FIG. 13 is a graphical presentation of the percentage of younger dogs successfully jumping over various heights relative to their individual shoulder height during four consecutive quarters of a 3 year period of feeding nutritionally-balanced compositions that provide mannoheptulose at levels of 0 mg/kg (Diet 1) or 2 mg/kg (Diet 2) of body weight of the dog. Jumping ability of individual dogs is determined quarterly as described herein below. The initial assessment (start of first quarter) is made at month 22 of the study and continues for one year. The four consecutive quarters are represented as reference numbers 30, 32, 34 and 36, respectively, of FIG. 13.

Table 8 shows least-squares means for measured shoulder heights of younger dogs fed Diet 1 and Diet 2 and the probability value of the pair-wise comparison between the two groups. Shoulder height of the individual dog is used herein below as the standard to assess individual jumping ability. The maximum height successfully jumped by an individual dog is expressed as a percentage of their individual shoulder height. A reported p-value greater than 0.10 indicates no significant difference in shoulder height for younger dogs assigned to Diet 1 and Diet 2.

TABLE 8

| Younger dogs | Diet 1 | Diet 2 | P-value |
| --- | --- | --- | --- |
| Shoulder height, cm | 21.8 | 22.5 | 0.123 |

Table 9 shows the probability value for the pair-wise comparison across all four quarters for the percentage of younger dogs fed Diet 1 and Diet 2 that successfully jump a height relative to their shoulder height. The assessment of functional capacity is based on the ability of younger dogs to successfully jump heights that range from 60 to 100% of their individual shoulder height. A reported p-value less than or equal to 0.10 indicates a statistically significant difference between Diet 1 and Diet 2 across all four test quarters for the percentage of dogs successfully jumping similar heights. A reported p-value that is greater than 0.10 indicates similar jumping ability for both groups across all four quarters.

TABLE 9

| | Jumping height as a percentage of shoulder height, % | | | | |
|---|---|---|---|---|---|
| | 60 | 70 | 80 | 90 | 100 |
| P-value comparing Diet 1 vs. Diet 2 | .001 | .664 | .362 | .531 | .959 |

A greater percentage of younger dogs can successfully jump heights that are typically considered non-strenuous for normal, healthy dogs (60 or 70% of their shoulder height). As jumping height increases to 80, 90 or 100% of their shoulder height a smaller percentage of younger dogs can successfully jump these heights demonstrating a more demanding and physically challenging activity and/or test for younger dogs. With the exception of 60% of their shoulder heights, the percentage of younger dogs that successfully jump required height is similar regardless of the consumption of a nutritionally-balanced composition providing a level of mannoheptulose of 0 or 2 mg/kg of body weight. Only at a non-strenuous height of 60% of the individual shoulder can a greater percentage of younger dogs consuming Diet 2 outperform dogs consuming Diet 1. The benefit of maintaining and/or attenuating a decline in jumping ability is not sustained at higher height levels signifying a similar level of jumping ability in both groups of younger dogs.

Figure 14:
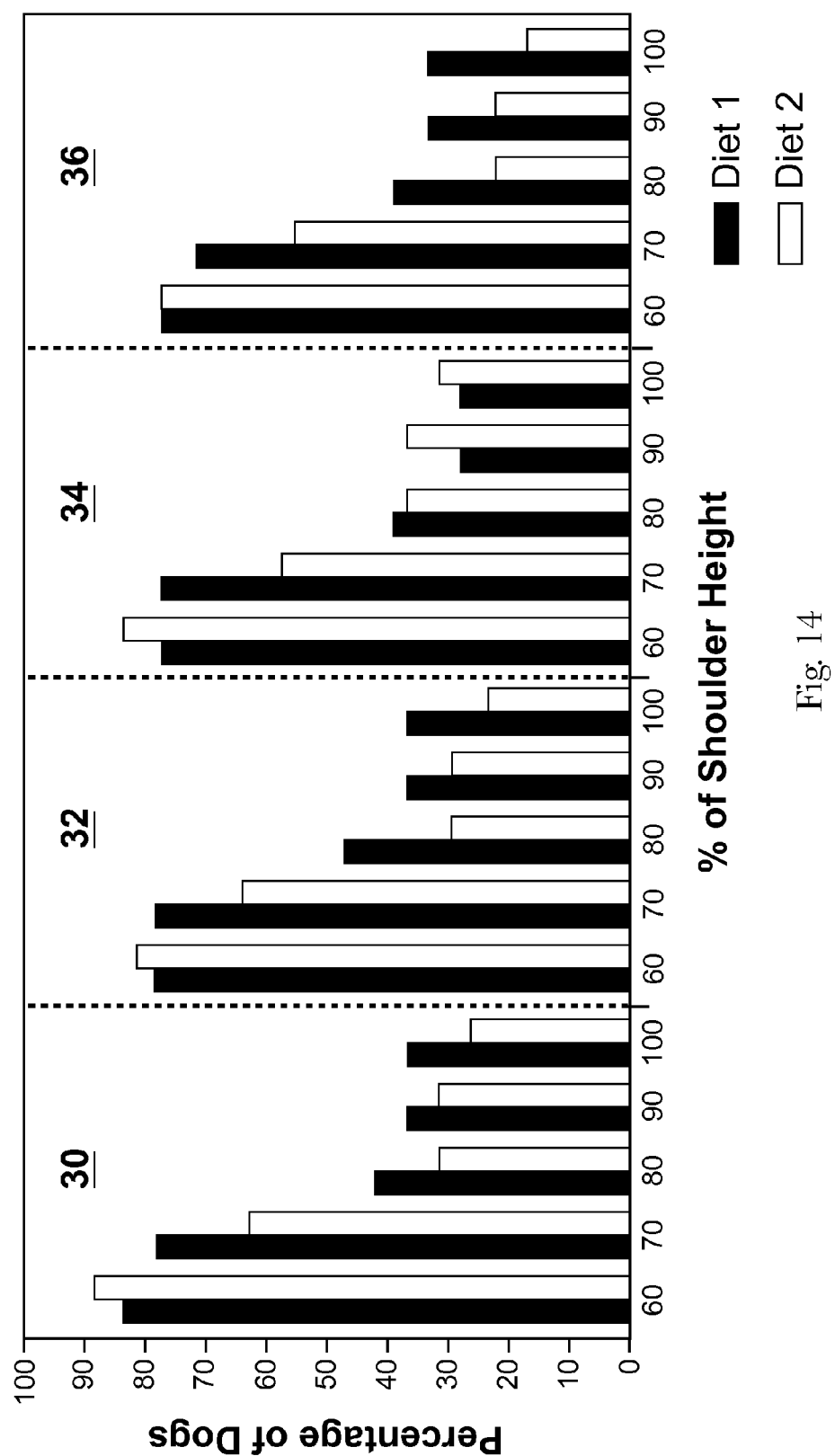
FIG. 14 is a graphical presentation of the percentage of younger dogs successfully jumping onto table platforms of various heights relative to their individual shoulder height over one year of a 3 year period of feeding nutritionally balanced compositions containing mannoheptulose at a dose of 0 or 2 mg/kg of body weight of the dog. Jumping ability is assessed during 4 consecutive quarters beginning in month 8.

FIG. 14 is a graphical presentation of the percentage of younger dogs successfully jumping onto table platforms of varying heights relative to their shoulder height during 3 years of feeding nutritionally-balanced compositions that provide mannoheptulose at levels of 0 mg/kg (Diet 1) or 2 mg/kg (Diet 2) of body weight of the dog. Jumping ability of individual dogs is determined quarterly as described herein below. The initial assessment (start of first quarter) is made at month 22 of the study and continues for one year. The four consecutive quarters are represented as reference numbers 30, 32, 34 and 36, respectively, of FIG. 14.

Table 10 shows the probability value for the pair-wise comparison across all four quarters for the percentage of younger dogs fed Diet 1 and Diet 2 that successfully jump onto table platforms of increasing height relative to their individual shoulder height. The assessment of functional capacity is based on the ability of younger dogs to successfully jump onto table platforms of differing heights that range from 60 to 100% of their individual shoulder height. A reported p-value less than or equal to 0.10 indicates a statistically significant difference between Diet 1 and Diet 2 across all four test quarters for the percentage of dogs successfully jumping onto table platforms of similar heights. A reported p-value that is greater than 0.10 indicates similar jumping ability for both groups across all four quarters.

TABLE 10

| | Platform height as a percentage of shoulder height, % | | | | |
|---|---|---|---|---|---|
| | 60 | 70 | 80 | 90 | 100 |
| P-value comparing Diet 1 vs. Diet 2 | .554 | .031 | .144 | .642 | .230 |

A greater percentage of dogs can successfully jump onto table platform heights that are typically considered non-strenuous for normal, healthy dogs (60 or 70% of their shoulder height). As the platform height increases to 80, 90 or 100% of their individual shoulder height, a smaller percentage of younger dogs can successfully jump onto taller platforms demonstrating a more demanding and physically challenging activity and/or test for younger dogs. With the exception of 70% of their shoulder heights, the percentage of younger dogs able to successfully jump onto platforms of a specific height is similar regardless of the consumption of a nutritionally-balanced composition providing a level of mannoheptulose of 0 or 2 mg/kg of body weight. Only at a non-strenuous height of 70% of the individual shoulder height can a greater percentage of younger dogs consuming Diet 1 outperform dogs consuming Diet 2. The benefit of maintaining and/or attenuating a decline in jumping ability is not sustained at higher height levels signifying a similar level of jumping ability in both groups of younger dogs.

The similarity in jumping ability of the younger dogs fed Diet 1 and Diet 2 is likely dependent on their current ages. It is accepted by those skilled in the art that younger dogs are more likely to perform most physical tests and subtle differences in ability are not noticeable at younger ages. It can be expected that the jumping ability of younger dogs consuming the composition devoid of mannoheptulose (Diet 1) cannot be sustained due to declines in lean body mass, bone mineral density, bone mineral content, and muscle strength. It is expected declines in lean body mass, bone mineral density, bone mineral content, and muscle strength will manifest as a decline in functional mobility of the younger dogs as they age.

METHODS

Animal Feeding Management

Dogs are subjected to a baseline period and fed a nutritionally-balanced composition devoid of mannoheptulose, avocado extract or avocado meal. The baseline feeding period is used to establish daily food allowance of individual dogs for maintaining ideal body weight and body condition ranges for each dog. An initial assessment by a licensed veterinarian determines the ideal range of body weight and body condition for each dog based on the breed standard for Labrador Retrievers and the body frame size of each dog. The daily food allowances can be adjusted as needed until the dog is within its ideal range of body weight and body condition. Once ideal body weight and body condition are achieved, the daily food allowance is fixed at that amount to maintain each dog within these ranges. The fixed daily food allowance is maintained during the remainder of the baseline period and the following test period. Adjustments to the fixed daily allowance may occur if the body condition of a dog falls outside an acceptable range of 2 to 4 as described in Table 11. Body condition score is evaluated quarterly according to criteria described in Table 11. The maximum allowable food adjustment for an individual dog is limited to +/−50 grams of food per day. The amount of this adjustment is dependent upon the dog's current body condition score relative to the preferred range of 2-4. The new food allowance is maintained for the next quarter before body condition scoring is repeated. This provision avoids large and rapid swings in food intake and helps to maintain each dog in a healthy and stable range of body weight and body condition through the feeding period.

TABLE 11

| Score | Description | Characteristics & Criteria |
|---|---|---|
| 1 | Extremely thin | Ribs, lumbar vertebrae, and pelvic bones visible at a distance and felt without pressure<br>No palpable fat over tail base, spine or ribs<br>Obvious absence of muscle mass<br>Severe concave abdominal tuck when viewed from side<br>Severe hourglass shape when viewed from above |
| 2 | Underweight | Ribs palpable with little pressure, may be visible<br>Minimal palpable fat over ribs, spine, tail base<br>Increased concave abdominal tuck when viewed from side<br>Marked hourglass shape to waist when viewed from above |
| 3 | Ideal | Ribs and spine palpable with slight pressure but not visible, no excess fat covering<br>Ribs can be seen with motion of dog<br>Good muscle tone apparent<br>Concave abdominal tuck when viewed from side<br>Smooth hourglass shape to waist when viewed from above |
| 4 | Overweight | Ribs palpable with slight excess fat covering which are difficult to feel with palpation<br>General fleshy, stout appearance<br>Abdominal concave tuck is decreased to absent when viewed from the side<br>Loss of hourglass shape to waist with back slightly broadened when viewed from above<br>Ribs not seen with motion of the dog |
| 5 | Extremely obese | Ribs and spine not palpable under a heavy fat covering<br>Fat deposits visible over lumbar area, tail base and spine<br>Abdomen is convex with or without a pendulous ventral bulge<br>Back is markedly broadened |

Dual Energy X-Ray Absorptiometer (DEXA)

Whole-body composition measures of lean mass, fat, bone mineral density, and bone mineral content of adult dogs are obtained using Dual Energy X-ray Absorptiometer (DEXA). DEXA scans of anesthetized dogs are performed by a registered veterinary technician or a licensed veterinarian using a Hologic Delphi QDR® Series X-ray Bone Densitometer (Model Delphi-A, Serial No. 70852; Bedford, Mass.). A quality control calibration is completed prior to the start of the scan and standard operating procedures are followed as described in the User's Guide for X-Ray Bone Densitometer with QDR® for Windows®.

Dogs are fasted for a minimum of 12 hours prior to time of anesthesia and the DEXA scan. Fasting body weights are collected prior to anesthesia and recorded. Standard veterinary techniques are followed to provide safe and effective induction, maintenance, and recovery of anesthesia using appropriate sedation and tranquilization procedures for the dogs. Anesthetic supplies including needles, syringes, and artificial tears are assembled, as well as endotracheal tubes of various sizes.

The dog is sedated using a pre-anesthetic combination of Acepromazine (0.55 mg/kg intramuscular injection] and Atropine (0.04 mg/kg subcutaneous injection), then placed on the DEXA table. The dog is anesthetized using Propofol (7 mg/kg) administered via a secured intravenous catheter. The dog is intubated with an endotracheal tube and delivered 100% oxygen. A gas anesthesia machine is available in the event Isoflurane needs to be administered should the dog begin to recover prior to the scan being completed. Vital signs including respiratory rate and pulse are collected following induction with Propofol (before scan) and immediately after the 90-second scan.

The dog is positioned on its sternum with the head and neck as straight as possible. The forelimbs are rotated caudally and positioned at the dog's side. The hind limbs are extended and placed as straight as possible. The tail is straightened and placed between the hind limbs. The spine is positioned by the technician to be as straight as possible when viewed from a head-on position. If necessary, the technician will correct any curvature to the dog's body by re-positioning the dog. The length of the dog is measured from the tip of the nose to about one inch past the tip of the rear foot using a tape measure. These data are entered into the Hologic QDR Series program, according to standard procedures in the User's Guide for X-Ray Bone Densitometer with QDR® for Windows®. 'Whole Body' is selected as the scan type. The C-arm on the DEXA unit makes three passes over the dog in about 90 seconds, at which time the scan is complete.

Following DEXA, anesthesia is discontinued at the end of the procedure. Oxygen continues to be delivered to the dog for at least five minutes prior to being disconnected from the machine. The dog is moved to a recovery cage where the endotracheal tube is removed once the dog regains its swallowing reflex.

DEXA provides whole-body measures of bone mineral density, bone mineral content, total fat, lean body mass, lean body mass+bone mineral content, total mass, and percentage (%) of fat. The percentage (%) of whole-body lean is calculated as 'Whole-Body Total Lean'/'Whole-Body Total Mass'×100.

Muscle Strength

Muscle strength, expressed as muscle power, of dogs is measured using a system comprised of a weight-pulling harness and a weight stack equipped with a pulley system. The following equipment is used to perform strength tests:

Dog weight-pulling harness: custom-made to a dog's body weight and body measurements; constructed of nylon material; a harness size for a typical adult Labrador Retriever, for example, will have a 25 inch circumference head hole with foam padding, and be 43 inches in length from center of neck to D-ring (PullDoggies.com)

Weight stack and pulley system: single pulley, free-standing, 150-pound weight stack, no boom (Therapy Systems; Roseville, Calif.) modified to accommodate a total weight of 75 pounds in 5 pound increments (additional 5 pound weights also by Therapy Systems)

Intercomp CS200 Force Meter (Intercomp Co.; Medina, Minn.)

Digital timer calibrated stop watch, model no. 61161-350 (Control Company, Friendswood, Tex.)

Turf spun roll, gray, 3 feet width×12 feet length×0.5 inches thickness, anti-fatigue matting (Scottissue, Inc.; Dayton, Ohio); customized by identifying length of matting in 0.10 meter increments using a permanent marking pen. A maximum pulling distance of 2.4 meters is also marked on the mat.

SitStay Clicker (SitStay, Inc.; Lincoln, Nebr.) positive reinforcement animal training clicker devices; or equivalent Encouragement devices (eg, toys, diet kibble as treats)

Prior to performing the first strength test, each dog undergoes a multi-step training and acclimation process to familiarize the dog with the harness and the act of pulling weights. A dog is fitted to the harness and wears it during normal activities in an outdoor play yard. Once the dog is comfortable wearing the harness, an empty 1-gallon milk jug is attached to the harness to desensitize the dog to noises and sensations associated with pulling something. Increasing amounts of weight are added to the milk jug by adding pebbles. The dog is ready to perform the test once it successfully exhibits normal activity and play while pulling the pebble-filled milk jug. Time required to complete the acclimation process can range from days to weeks, depending on the personality of the individual dog.

All dogs are clicker trained. Clicker training is an animal training method based on behavioral psychology that relies on marking desirable behavior and rewarding it. Desirable behavior is marked by using a clicker, a mechanical device that makes a short, distinct 'click' sound, which tells the animal exactly when it is doing the right thing. This clear form of communication, combined with positive reinforcement, is an effective, safe, and humane way to teach any animal any behavior that it can physically and mentally perform. The human trainer clicks at the moment the behavior occurs, then delivers an appropriate reward (eg, food, human interaction, toy). Once dogs are trained, the clicker may no longer be needed on a daily basis, however, rewards are continued as positive reinforcement.

After dogs are trained and acclimated to the harness, pull weights, and the clicker positive reinforcement technique, a minimum of two technicians perform the two phases of the strength test: the step-up pull test and the repetition pull test. Each dog is fitted with a weight-pulling harness, which is then hooked to the weight stack and pulley system. Maximum peak pulling force is collected using a calibrated Intercomp CS200 Force Meter, operated according to standard operating procedures as described in Intercomp CS200 Users Manual. The force meter is reset after each pull attempt. Maximum peak pulling force is recorded but is not used in the calculation of work or power.

A step-up pull test is performed first. A successful pull is defined as the weight a dog can pull a distance of 2.4 meters within 30 seconds. One technician serves as the dog's handler and encourages the dog to begin pulling using various encouragement devices (eg, toys, diet kibble as treats, and/or vocal praise). At no time does the technician touch the dog to provide assistance. The second technician zeros the force meter and starts the stop watch when the dog takes its first step. When the dog reaches the 2.4 meter line the technician supports the pulled weight, to prevent the dog from being drawn backwards, while stopping the stop watch. The pull weight (lbs), pulling distance (2.4 m), elapsed time (s) and maximum peak pulling force (kg-force) are recorded by the technician. Weights are increased in five-pound increments (up to a maximum 75 pounds) until the dog is unsuccessful in completing the pull within the allotted distance and time. If a dog does not reach the 75-lb maximum, the pull weight, pulling distance, elapsed time and maximum peak pulling force are recorded for the final unsuccessful pull.

Upon completion of the step-up test, a repetition pull test is then performed. The pulling weight for the repetition test is returned to the maximum weight successfully pulled by the dog during the step-up pull test. Utilizing positive reinforcement, the dog pulls this same weight for a maximum of 10 times over the same 2.4 meter distance. Each repetitive pull must be completed within 30 seconds to be considered a successful pull. The time required to pull the weight the 2.4 meter distance is collected using the stop watch and recorded for each repetition. Maximum peak pulling force is recorded but is not used in the calculation of work or power. If a dog cannot perform all 10 repetitive pulls, the pull weight, pulling distance, elapsed time and maximum peak pulling force are recorded for the final unsuccessful pull.

Data collected are used to calculate the work performed and power exerted by each dog during each individual pull using the following equations.

$$Force(newtons) = Mass \times Acceleration$$

$$Mass(kg) = \text{individual weight successfully pulled by dog}$$

$$Acceleration = 9.80665 \text{ m/s}^2$$

$$Work(joules) = Force \times Distance(m)$$

$$Power(watts) = Work/Time(s)$$

Total work and total power are calculated for each dog by summing all individual step-up and repetition pulls into an overall measure of muscle strength.

Activities of Daily Living

Activities of daily living (ADL) measurements can be collected utilizing activities such as jumping onto platform tables (ADL-Table) or jumping over hurdles (ADL-Jump). These activities allow dogs to demonstrate their agility and ability to perform normal daily tasks. Activity measurements are designed to mimic common actions of dogs in a home environment and which typically become more difficult to perform as dogs age. A minimum of two technicians is required to conduct each activity test. One technician serves as the dog handler and one technician records data.

Prior to data collection, technicians train all dogs to perform the activities by using positive encouragement and reinforcement training techniques, such as clicker training as described previously. Dogs are guided through each activity by a handler who uses encouragement devices (eg, toys, diet kibbles as treats) and/or vocal praise. At no time does the handler touch the dog to provide assistance.

Figure 15:
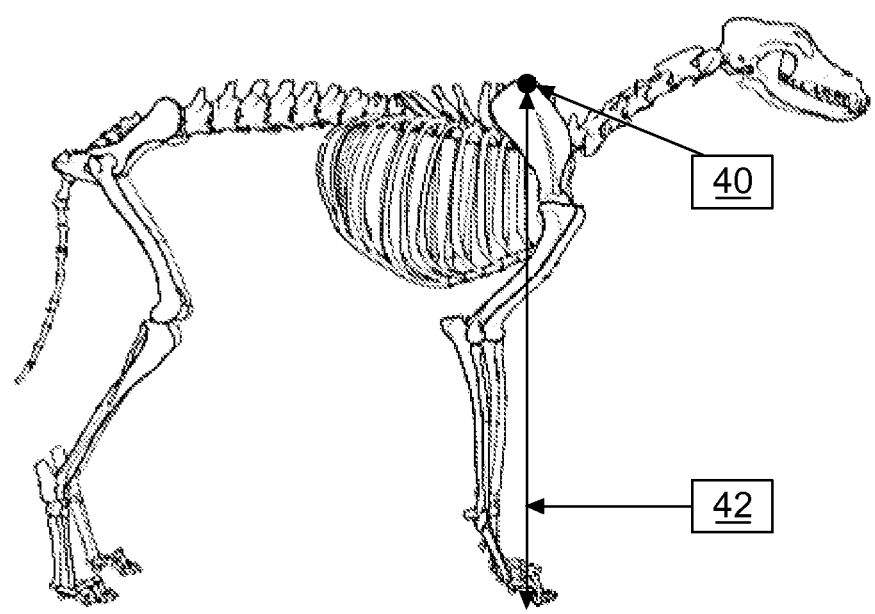
FIG. 15 is a right side view of a skeleton of a dog.

Shoulder height of each individual dog is measured using a tape measure and recorded. Shoulder height is defined as the distance 42 between the bottom of the right front leg (ground) to the proximal point of the scapular spine 40, as illustrated in FIG. 15.

The ADL-Table activity requires the dog to jump on to and down from the platform of four tables of graduated heights, starting with the lowest table height first. The ADL-Jump activity requires the dog to jump over a hurdle of incrementally increasing bar heights. Each of these two activities is described in more detail below. For both activities, dogs are scored for the number of attempts at each graduated height and the successful completion of each height.

The ADL-Table activity is conducted indoors in a room equipped with the following equipment:

One table ('Low') constructed of welded aluminum with skid-proof paint applied to a 3 feet×3 feet platform top (Agility-Equipment.com; Goffstown, N.H.). Height of Low table is 7 inches from the floor to the top of the platform surface.

One table ('Medium') constructed of welded aluminum with skid-proof paint applied to a 3 feet×3 feet platform top (Agility-Equipment.com; Goffstown, N.H.). Height of Medium table is 12 inches from the floor to the top of the platform surface.

One table ('High') constructed of welded aluminum with skid-proof paint applied to a 3 feet×3 feet platform top (Agility-Equipment.com; Goffstown, N.H.). Height of High table is 16 inches from the floor to the top of the platform surface.

One table ('Highest') constructed of welded aluminum with skid-proof paint applied to a 3 feet×3 feet platform top (Agility-Equipment.com; Goffstown, N.H.). Height of Highest table is 24 inches from the floor to the top of the platform surface.

Turf spun roll, gray, 0.5 inches thickness, anti-fatigue matting (Scottissue, Inc.; Dayton, Ohio)

Encouragement devices (eg, toys, assigned diet kibbles for treats)

Leashes

All tables are placed on gray matting to provide a non-slick and cushioned floor surface for the dogs. The mat (3 feet width×15 feet length) provides some protective cushioning for the dogs as they jump up onto and down from each table. A second mat (3 feet width×14.5 feet length) is stacked on top of the first mat and placed in front of the Medium, High and Highest tables for extra cushioning.

To perform the ADL-Table activity, the handler walks the dog on leash to the Low table. The handler may lightly hold on to the leash during the activity, depending upon the dog. The dog is encouraged to jump or climb on to the table using vocal praise, toy or treat. After jumping onto the platform the dog is encouraged to return to the floor by jumping or climbing down from the table. The dog is provided with two attempts to perform both activities to receive a successful score. The assessor records 'Yes' if the dog successfully jumps onto the structure and then jumps back to the floor. A "No" is recorded if the dog does not perform the task as described or makes no attempt to jump on to or from the structure. The number of attempts (1 or 2) is also recorded. If the dog successfully completes the activity at the Low table on its first or second attempt, the handler moves the dog immediately to the Medium table and repeats the same procedure. If the dog successfully completes the activity at the Medium table, the handler moves the dog immediately to the High table and repeats the same procedure. If the dog successfully completes the activity at the High table, the handler moves the dog immediately to the Highest table and repeats the same procedure. The test is completed when the dog successfully completes the activity on the Highest table or receives a "No" score on the two attempts for a structure. The highest platform table height successfully achieved by the dog is recorded. The highest successful height (inches) for a dog is expressed as a percentage of its measured shoulder height (inches).

The ADL-Jump activity is conducted indoors in a room equipped with the following:

Aluminum hurdle (jump) structure (Agility-Equipment.com; Goffstown, N.H.), 4 feet wide and fitted with slots for horizontal bars at the following heights (measured from the floor to the top of the bar):
Level 1=7 inches
Level 2=11 inches
Level 3=15 inches
Level 4=19 inches
Level 5=21 inches
Level 6=23 inches
Level 7=25 inches Seven PVC pipes, ¾ inches diameter×4 feet length that function as removable horizontal hurdle bars Turf spun roll, gray, 0.5 inches thickness, anti-fatigue matting (Scottissue, Inc.; Dayton, Ohio)

Encouragement devices (ie, toys, assigned diet kibbles for treats)

The hurdle structure is placed on gray matting to provide a non-slick and cushioned floor surface for the dogs. Two mats (4.5 feet width×15 feet length) are double-stacked to provide a runway, jumping and landing areas with extra cushion as dogs perform this activity.

To perform the ADL-Jump activity, a hurdle bar is placed at the Level 1 position. The handler walks the dog on leash to a distance on the runway of approximately 6 to 8 feet from the hurdle. The dog is encouraged to jump over the hurdle using vocal praise, toy or treat. The handler does not touch the dog immediately before or during the activity. The handler may lightly hold on to the leash during the activity, depending upon the dog. To receive a successful score the dog must jump over the hurdle, without knocking the bar down, in no more than two attempts. The dog has two attempts to successfully jump over the hurdle. The assessor records 'Yes' if the dog successfully jumps the height without knocking the bar down. A score of 'No' is recorded if the dog does not attempt to jump the height or knocks the bar down. The number of attempts (1 or 2) is also recorded. If the dog successfully completes the Level 1 hurdle in its first or second attempt, a second hurdle bar is placed at the Level 2 and immediately repeats the same procedure. The same process is followed up to the Level 7 position or until the dog is unsuccessful in its two attempts at a specific height. The highest hurdle height successfully achieved by the dog is recorded. The highest successful height (inches) for a dog is expressed as a percentage of its measured shoulder height (inches).

High Performance Liquid Chromatography Tandem Mass Spectometry (LC/MS/MS):

High performance liquid chromatography tandem mass spectrometry (HPLC/MS/MS) is utilized to determine the amount of mannoheptulose present in the plasma of adult dogs. D-mannoheptulose and its chemical analog internal standard ($D_7$-glucose) are isolated from dog plasma by a protein precipitation procedure (described herein below) using a 96-well format. The analyte and internal standard are subjected to reverse-phase high performance liquid chromatographic (HPLC) analysis on a polymeric amino column (2.1×150 mm, 5-μm particles). Detection and quantitation is by mass spectrometry (MS) operating under multiple reaction monitoring MS/MS conditions. Concentrations of D-mannoheptulose in dog plasma can be quantitated from approximately 20 to 5000 ng/mL. The assay requires a 0.1 mL aliquot of dog plasma harvested from a $Na_2EDTA$ anti-coagulant blood collection tube. Specimen concentrations are determined by back-calculation using a weighted ($1/x^2$) linear regression of a calibration curve generated from prepared D-mannoheptulose calibration standards.

The following reagents and apparatus are used to perform the analyses:

Reagents

D-mannoheptulose Analytical Reference External Standard. Carbosynth, Compton-Berkshire, UK.

D-glucose-1,2,3,4,5,6,6-d7 ($D_7$-glucose), Method Reference Internal Standard (IS). Cambridge Isotope Laboratories, Andover Mass.

Acetonitrile (ACN). HPLC solvent; or equivalent

Formic Acid (FA), 88%, A.C.S. Reagent; or equivalent
Analytical Reagent Grade Water (ARW); or equivalent
Unfiltered Control (Blank) Dog Plasma with $Na_2EDTA$ anti-coagulant. Bioreclamation; or equivalent
Needle Wash 1: (10:90) ACN:ARW with 0.05% FA
Needle Wash 2: (95:5) ACN:ARW with 0.1% FA
Mobile Phase A: ARW with 0.1% FA
Mobile Phase B: ACN with 0.1% FA Apparatus Electronic Dispensing Pipettes (EDP), manual pipettes
HPLC pump. Shimadzu (Shimadzu; Kyoto, Japan) Model SCL-10A vp system controller & LC-10AD vp pumps with Gilson Model 811C mixer (65 µL volume)
Mass spectrometer. Sciex (Applied Biosystems/MDS SCIEX; Foster City, Calif.) API 4000 Q-Trap or instrument meeting equivalent sensitivity requirements using analyst software
Two Position Actuator. Valco Instruments Company Inc; Houston, Tex.)
Analytical Column. apHera $NH_2$ column (Sigma-Aldrich; St. Louis, Mo.), 2.1×150 mm (3 µm particle)
Screw Cap with Silicone O-Ring. VWR Scientific Products (West Chester, Pa.) Cat. No. 20170-241
Polypropylene Vials, Skirted Conical, Natural. 0.5 mL & 2 mL screw cap tubes with cap
Multi-Tube Vortexer. VWR Scientific Products (West Chester, Pa.) brand; or equivalent.
1.3 mL Round Well Round Bottom Polypropylene 96-well extraction/injection plates. (Microliter Analytical Supplies Inc; Suwanee, Ga.; Cat. No. 07-3000); or equivalent
Sealing Mat for 1.3 mL Deep 96 Round Well Collection Plates. (Whatman Polyfiltronics; Rockland, Md.; Cat. No. 7704-0105); or equivalent
Autosampler. CTC Analytics HTS PAL (Leap Technologies; Carrboro, N.C.); or equivalent
Centrifuge. Beckman Coulter (Beckman Coulter; Fullerton, Calif.) Alleger X-15 with Microplate Carrier and SX4750A Rotor; or equivalent Procedure 1. Preparation of D-Mannoheptulose Standard Stock Solution and Calibration Standards:

Prepare 0.500±0.100 mg/mL stock solutions of the D-mannoheptulose Analytical Reference External Standard in ARW water. Store the solutions in polypropylene vials at 2-4° C. until use. For each assay, prepare fresh D-mannoheptulose calibration standards using D-mannoheptulose stock solution and ARW water for final concentrations of 0.2, 0.4, 0.8, 2, 4, 8, 20, 40 and 50 ug/mL.

2. Preparation of $D_7$-Glucose Internal Standard (IS) Solutions

Stock $D_7$-Glucose (IS) Solution (1000 ug/mL):

Prepare 1.000±0.100 mg/mL solutions of $D_7$-glucose_Method Reference Standard in ARW water. Store the solutions in polypropylene vials at or below −70° C. until use.

Working IS Solution (~25 µg/mL):

Prepare 25 ug/mL solution using stock IS solution and ARW water. Store the solution at approximately 4° C. until use. The solution expires after 3 months.

3. Batch Preparation:

A study batch includes calibration standards, quality control (QC) samples, appropriate blanks, and study specimens. Samples can be transferred to their appropriate location in the 96-well plate manually. A study batch can contain a maximum of 96 samples, including calibration standards, QC samples, blanks and study specimens. Specimen and QC samples are thawed at room temperature.

Calibration Standards. Transfer 0.100 mL of each freshly-prepared calibration sample into its assigned position in the 96-well extraction plate.

Study Specimens and QC Samples. Samples are allowed to thaw at room temperature before pipetting. Dilute as necessary using ARW water. Transfer 0.100 mL of each sample into its assigned position in the 96-well extraction plate.

Blanks. Pipette 0.100 mL of ARW water into the reagent blank assigned position in the 96-well extraction plate. Pipette 0.100 mL of the appropriate control dog plasma into the positions assigned to plasma blank and zero standard.

Add 0.025 mL of ARW water to the Blank positions.

Add 0.025 mL of Working IS Solution to all positions of the 96-well extraction plate except the blank positions. Cover and vortex the plate for ~15 seconds.

Add 0.500 mL of acetonitrile to all positions of the 96-well extraction plate for protein precipitation. Cover and vortex the plate for ~15 seconds and then centrifuge at ~3000 RPM for ~10 minutes.

Transfer 0.400 mL of the supernatant from the 96-well extraction plate to the 96-well injection plate. Concentrate the supernatant to about 0.2 mL by nitrogen purge. Cover the 96-well injection plate and vortex for ~15 seconds.

Analyze all samples by HPLC/MS/MS analysis according to equipment specifications as described below.

Analysis

To perform the analysis by HPLC/MS/MS, the instrument parameters listed below are used to analyze approximately 10 µL of each of the samples in the batch. From the MS data acquisition system, obtain the peak areas (PA) for D-mannoheptulose and internal standard in each sample.

| HPLC Parameters - API 4000 Q-Trap Sciex MS with Shimadzu Pump and Leap Injector | |
| --- | --- |
| Flow rate | 350 µL/min |
| Injection volume | 10 µL (the injection volume may be adjusted to optimize the HPLC/MS/MS sensitivity) |
| Run time (analyte retention) | 6.0 min (~3.3 min for analyte and IS) |
| Mobile Phase A | ARW with 0.1% Formic Acid |
| Mobile Phase B | ACN with 0.1% Formic Acid |
| Needle wash 1 | (10:90) ACN:ARW with 0.05% Formic Acid |
| Needle wash 2 | (95:5) ACN:ARW with 0.1% Forminc Acid |
| HPLC Column Temperature | Ambient |

| Gradient | | | |
| --- | --- | --- | --- |
| Time | Mobile Phase A (%) | Mobile Phase B (%) | Divert Valve |
| 0.0 | 25 | 75 | To Waste |
| 0.1 | 25 | 75 | |
| 1.0 | | | To MS |
| 3.5 | 35 | 65 | |
| 3.51 | 50 | 50 | |
| 4.5 | 50 | 50 | |
| 4.5 | | | To Waste |
| 4.51 | 25 | 75 | |

Following are typical operating conditions (parameters) for the Sciex API 4000 Q-Trap mass spectrometers. These parameters may be adjusted to optimize the response; however, these parameters cannot be adjusted during a run, but rather a consistent set of instrument settings/parameters must be used for each run.

| Mass Spectrometer Parameters | |
| --- | --- |
| Mass Spectrometer: | Sciex API 5000 |
| Ionization mode: | Turbo-Ion Spray-ESI |
| Polarity: | Negative |
| Turbo Temp: | 350° C. |
| CUR: | 45 |
| GS 1: | 35 |
| GS 2: | 60 |
| IS: | −3500 |
| CAD: | High |
| DP: | −25 |
| EP: | −11 |
| CE: | −10 |
| CXP: | −7 |

| Ions used in MRM mode | | |
| --- | --- | --- |
| Compound | Parent Ion (m/z) | Product Ion (m/z) |
| D-mannoheptulose | 255.0 | 209.0 |
| D$_7$-glucose | 232.0 | 186.0 |

A weighted ($1/x^2$) linear regression analysis for D-mannoheptulose in the calibration standards is performed in Watson LIMS, for the observed signal (defined here as the peak area ratio of each analyte to its internal standard) as a function of the analyte concentrations. The concentration of the analyte in the calibration standards, QC samples and study specimens is then back-calculated using the generated regression equation resident in Watson LIMS.

Run acceptance is assessed through evaluation of the standard calibration curve and QC sample read backs and satisfaction of the system suitability requirements that follow.

System suitability is assessed using performance qualification (PQ) solutions. PQ solution preparations are as follows:

Zero PQ=STD 0 from a sample set is used as a zero PQ.
Low PQ=the lowest standard from a sample set is used as a low PQ.
High PQ=the highest standard from a sample set is used as a high PQ.

Standards from single or various sample runs may be combined to make a PQ solution. The PQ samples are stored at ~11° C. and are stable for the duration of the process stability.

A zero performance qualification (PQ) solution injection is first made followed by an injection of the low PQ solution. Instrument sensitivity is assured by detection of the analyte in the low PQ solution at a Signal to Noise (S/N) ratio of >4. Moreover, this detection indicates that each quadrupole, Q1 and Q3, is properly calibrated to transmit and detect the proper parent (Q1) and product (Q3) ions of the species being monitored. The high PQ solution is next injected followed by repeated injections of the zero PQ solution. The absence of carryover is assured by the lack of excessive ion current for the analyte in the last zero PQ solution injection (should be <35% of that signal seen in the low PQ solution injection). A response greater than 35% would warrant injector cleaning procedures, etc. prior to proceeding to specimen analysis.

Zero standards (control plasma), plasma matrix blanks and reagent blanks are analyzed for diagnostic purposes. Results from these analyses are not directly employed to determine run acceptance. However, no response >10% of the largest internal standard response seen in the zero standard injection(s) should appear at the known retention time of the internal standard in either of the control plasma or reagent blanks. In addition, at least one of the zero standards (control plasma) should not yield ion current at the retention time of the analyte that exceeds 50% of that response seen in the low standard injection.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of maintaining and/or attenuating a decline in the quality of life of a cat of dog, said method comprising the step of orally administering to said cat or dog a composition comprising an effective amount of mannoheptulose wherein said effective amount of mannoheptulose provides a dosage to said cat or dog on a daily basis from about 0.001 gram per kilogram of body weight of said cat or dog to about 0.02 gram per kilogram of body weight of said cat or dog, wherein said maintaining and/or attenuating a decline in the quality of life of said cat or dog is selected from the group consisting of maintaining and/or attenuating a decline in whole body composition, maintaining and/or attenuating a decline in functional mobility, and combinations thereof.

2. The method of claim 1 wherein said composition is nutritionally balanced.

3. The method of claim 1 wherein said composition is a treat.

4. The method of claim 1 wherein said composition is at least partially extruded.

5. The method of claim 1 wherein said effective amount of mannoheptulose provides a dosage to said cat or dog on a daily basis from about 1 mg to about 15 mg per kg of body weight of said cat or dog.

6. The method of claim 5 wherein said effective amount of mannoheptulose provides a dosage to said cat or dog on a daily basis from about 2 mg to about 10 mg per kg of body weight of said cat or dog.

7. The method of claim 6 wherein said effective amount of mannoheptulose provides a dosage to said cat or dog on a daily basis from about 2 mg to about 5 mg per kg of body weight of said cat or dog.

8. A method of maintaining and/or attenuating a decline in whole body composition in a cat or dog, the method comprising the step of orally administering to said mammal a composition comprising an effective amount of mannoheptulose wherein said effective amount of mannoheptulose provides a dosage to said cat or dog from about 0.001 gram per kilogram of body weight of said cat or dog to about 0.02 gram per kilogram of body weight of said cat or dog per day.

9. The method of claim 8 wherein said composition is nutritionally balanced.

10. The method of claim 8 wherein said composition is a treat.

11. The method of claim 8 wherein said composition is at least partially extruded.

12. The method of claim 8 wherein said maintaining and/or attenuating a decline in whole body composition is maintaining and/or attenuating a decline in musculoskeletal health of said cat or dog.

13. The method of claim 8 wherein said effective amount of mannoheptulose provides a dosage to said cat or dog on a daily basis from about 1 mg to about 15 mg per kg of body weight of said cat or dog.

14. The method of claim 13 wherein said effective amount of mannoheptulose provides a dosage to said cat or dog on a daily basis from about 2 mg to about 10 mg per kg of body weight of said cat or dog.

15. The method of claim 14 wherein said effective amount of mannoheptulose provides a dosage to said cat or dog on a daily basis from about 2 mg to about 5 mg per kg of body weight of said cat or dog.

16. A method of maintaining and/or attenuating a decline in musculoskeletal health in a cat or dog, said method comprising the step of orally administering to said cat or dog a composition comprising an effective amount of mannoheptulose wherein said effective amount of mannoheptulose provides a dosage to said cat or dog from about 0.001 gram per kilogram of body weight of said cat or dog to about 0.02 gram per kilogram of body weight of said cat or dog per day.

17. The method of claim 16 wherein said composition is nutritionally balanced.

18. The method of claim 16 wherein said composition is a treat.

19. The method of claim 16 wherein said composition is at least partially extruded.

20. The method of claim 16 wherein said maintaining and/or attenuating a decline in musculoskeletal health is selected from the group consisting of maintaining and/or attenuating a decline in muscle health, maintaining and/or attenuating a decline in skeletal health and combinations thereof.

21. The method of claim 20 wherein said maintaining and/or attenuating a decline in muscle health is selected from the group consisting of maintaining and/or attenuating a decline in lean body mass of said cat or dog, maintaining, enhancing and/or attenuating a decline in muscle strength, and combinations thereof.

22. The method of claim 20 wherein said maintaining and/or attenuating a decline in skeletal health is selected from the group consisting of maintaining and/or attenuating a decline in bone mineral density, maintaining, enhancing, and/or attenuating a decline in bone mineral content, and combinations thereof.

23. The method of claim 16 wherein said effective amount of mannoheptulose provides a dosage to said cat or dog on a daily basis from about 1 mg to about 15 mg per kg of body weight of said cat or dog.

24. The method of claim 23 wherein said effective amount of mannoheptulose provides a dosage to said cat or dog on a daily basis from about 2 mg to about 10 mg per kg of body weight of said cat or dog.

25. The method of claim 24 wherein said effective amount of mannoheptulose provides a dosage to said cat or dog on a daily basis from about 2 mg to about 5 mg per kg of body weight of said cat or dog.

26. A method of maintaining and/or attenuating a decline in the functional mobility of a cat or dog, the method comprising the step of orally administering to said cat or dog a composition comprising an effective amount of mannoheptulose wherein said effective amount of mannoheptulose provides a dosage to said cat or dog from about 0.001 gram per kilogram of body weight of said cat or dog to about 0.02 gram per kilogram of body weight of said cat or dog per day.

27. The method of claim 26 wherein said composition is nutritionally balanced.

28. The method of claim 26 wherein said composition is a treat.

29. The method of claim 26 wherein said composition is at least partially extruded.

30. The method of claim 26 wherein said effective amount of mannoheptulose provides a dosage to said cat or dog on a daily basis from about 1 mg to about 15 mg per kg of body weight of said cat or dog.

31. The method of claim 30 wherein said effective amount of mannoheptulose provides a dosage to said cat or dog on a daily basis from about 2 mg to about 10 mg per kg of body weight of said cat or dog.

32. The method of claim 31 wherein said effective amount of mannoheptulose provides a dosage to said cat or dog on a daily basis from about 2 mg to about 5 mg per kg of body weight of said cat or dog.

33. The method of claim 26 wherein said maintaining and/or attenuating a decline in the functional mobility of said cat or dog is maintaining and/or attenuating a decline in the activities of daily living of said cat or dog.

34. The method of claim 26 wherein said maintaining and/or attenuating a decline in the functional mobility of said cat or dog is maintaining and/or attenuating a decline in the jumping ability of said cat or dog.

* * * * *